United States Patent
Keren

(10) Patent No.: US 10,226,340 B2
(45) Date of Patent: Mar. 12, 2019

(54) CARDIAC PROSTHESES AND THEIR DEPLOYMENT

(71) Applicant: THE MEDICAL RESEARCH, INFRASTRUCTURE AND HEALTH SERVICES FUND OF THE TEL AVIV MEDICAL CENTER, Tel Aviv (IL)

(72) Inventor: Gad Keren, Kiryat Ono (IL)

(73) Assignee: THE MEDICAL RESEARCH, INFRASTRUCTURE AND HEALTH SERVICES FUND OF THE TEL AVIV MEDICAL CENTER, Tel Aviv (IL)

( * ) Notice: Subject to any disclaimer, the term of this patent is extended or adjusted under 35 U.S.C. 154(b) by 243 days.

(21) Appl. No.: 15/027,699

(22) PCT Filed: Oct. 8, 2014

(86) PCT No.: PCT/IB2014/065147
§ 371 (c)(1),
(2) Date: Apr. 7, 2016

(87) PCT Pub. No.: WO2015/052663
PCT Pub. Date: Apr. 16, 2015

(65) Prior Publication Data
US 2016/0242901 A1  Aug. 25, 2016

Related U.S. Application Data

(60) Provisional application No. 61/888,048, filed on Oct. 8, 2013.

(51) Int. Cl.
*A61F 2/24* (2006.01)
*A61F 2/95* (2013.01)

(52) U.S. Cl.
CPC ............ *A61F 2/243* (2013.01); *A61F 2/2409* (2013.01); *A61F 2/2418* (2013.01);
(Continued)

(58) Field of Classification Search
CPC ...... A61F 2/243; A61F 2/2409; A61F 2/2418; A61F 2/2436; A61F 2/2427; A61F 2/24;
(Continued)

(56) References Cited

U.S. PATENT DOCUMENTS 7,195,641 B2 * 3/2007 Palmaz ................. A61F 2/2418
623/1.26
2005/0137689 A1 * 6/2005 Salahieh ............... A61F 2/2418
623/2.11
(Continued)

FOREIGN PATENT DOCUMENTS

CN 101180010 5/2008
CN 102438546 5/2012
(Continued)

OTHER PUBLICATIONS

Extended European Search Report for Corresponding European Application 14852328.5 dated Jun. 9, 2017.
(Continued)

*Primary Examiner* — Jocelin Tanner
(74) *Attorney, Agent, or Firm* — A.C. Entis—IP Ltd.; Allan C. Entis

(57) ABSTRACT

A method of replacing a native cardiac valve with a prosthetic cardiac valve, the method comprising: expanding a wire mesh scaffolding in a chamber of the heart on a retrograde side of the native cardiac valve; while the scaffolding is expanded on the retrograde side of the valve positioning the prosthetic cardiac valve at the site of the native cardiac valve; expanding the prosthetic cardiac valve to replace the native cardiac valve; and collapsing the
(Continued)

scaffolding to a collapsed state and removing the collapsed scaffolding from the chamber of the heart.

20 Claims, 27 Drawing Sheets

(52) U.S. Cl.
CPC .... *A61F 2/2436* (2013.01); *A61F 2002/9517* (2013.01); *A61F 2230/001* (2013.01); *A61F 2230/008* (2013.01); *A61F 2230/0065* (2013.01); *A61F 2230/0069* (2013.01); *A61F 2230/0078* (2013.01); *A61F 2230/0093* (2013.01)

(58) Field of Classification Search
CPC ........ A61F 2002/9517; A61F 2230/001; A61F 2230/0065; A61F 2230/0069; A61F 2230/0078; A61F 2230/008; A61F 2230/0093

See application file for complete search history.

(56) References Cited

U.S. PATENT DOCUMENTS

| | | | | |
|---|---|---|---|---|
| 2007/0112374 | A1* | 5/2007 | Paul | A61F 2/013 606/200 |
| 2008/0228209 | A1* | 9/2008 | DeMello | A61B 17/221 606/159 |
| 2009/0287290 | A1 | 11/2009 | Macaulay et al. | |
| 2010/0191326 | A1* | 7/2010 | Alkhatib | A61F 2/013 623/2.11 |
| 2010/0217382 | A1* | 8/2010 | Chau | A61F 2/2418 623/1.26 |
| 2010/0262231 | A1* | 10/2010 | Tuval | A61F 2/2412 623/2.4 |
| 2011/0264196 | A1 | 10/2011 | Savage et al. | |
| 2012/0053682 | A1* | 3/2012 | Kovalsky | A61F 2/2418 623/2.11 |
| 2012/0095549 | A1 | 4/2012 | Forster et al. | |
| 2012/0303113 | A1 | 11/2012 | Benichou et al. | |
| 2014/0066969 | A1* | 3/2014 | Eskridge | A61B 17/221 606/200 |

FOREIGN PATENT DOCUMENTS

| | | |
|---|---|---|
| CN | 102869317 | 1/2013 |
| JP | 2010220834 | 10/2010 |
| WO | 2012012761 | 1/2012 |
| WO | 2013037519 | 3/2013 |
| WO | 2013059776 | 4/2013 |

OTHER PUBLICATIONS

Chinese Office Action for Corresponding Application No. 2014800670092, dated Feb. 4, 2017, filed Jun. 7, 2016.

PCT Search Report dated Feb. 15, 2015 for corresponding PCT Application PCT/IB2014/065147 filed Oct. 8, 2014.

Office Action dated Oct. 25, 2017 for Corresponding Chinese Application 2014800670092 filed Jun. 7, 2016.

\* cited by examiner

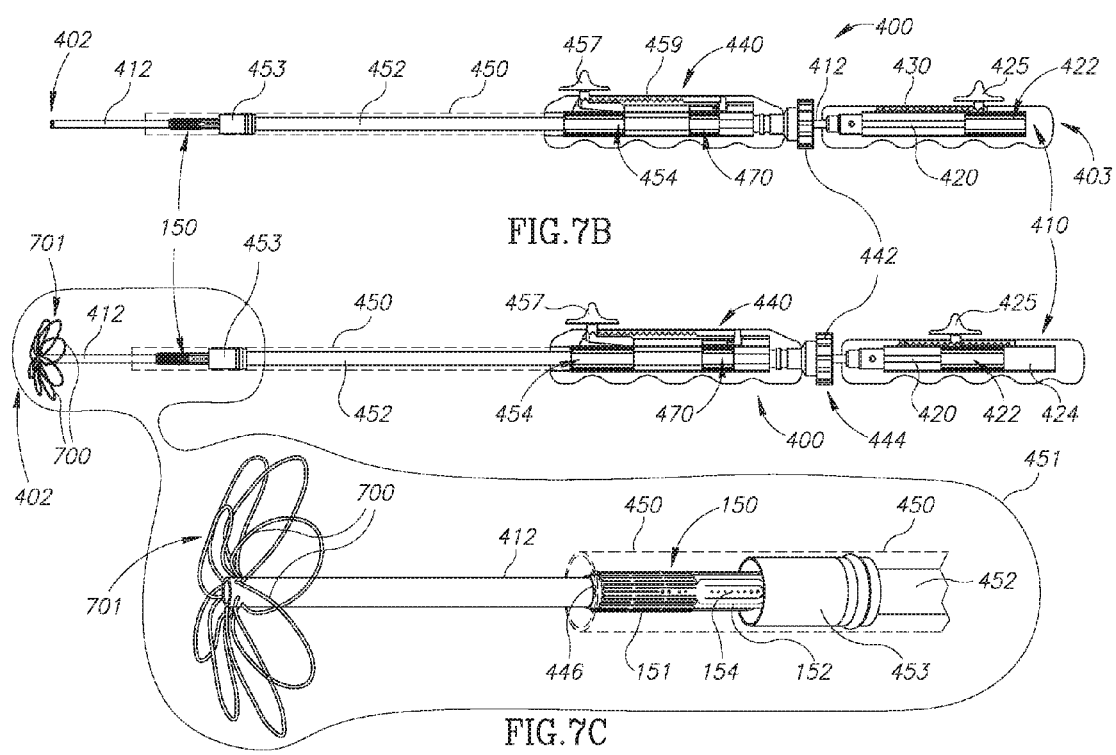

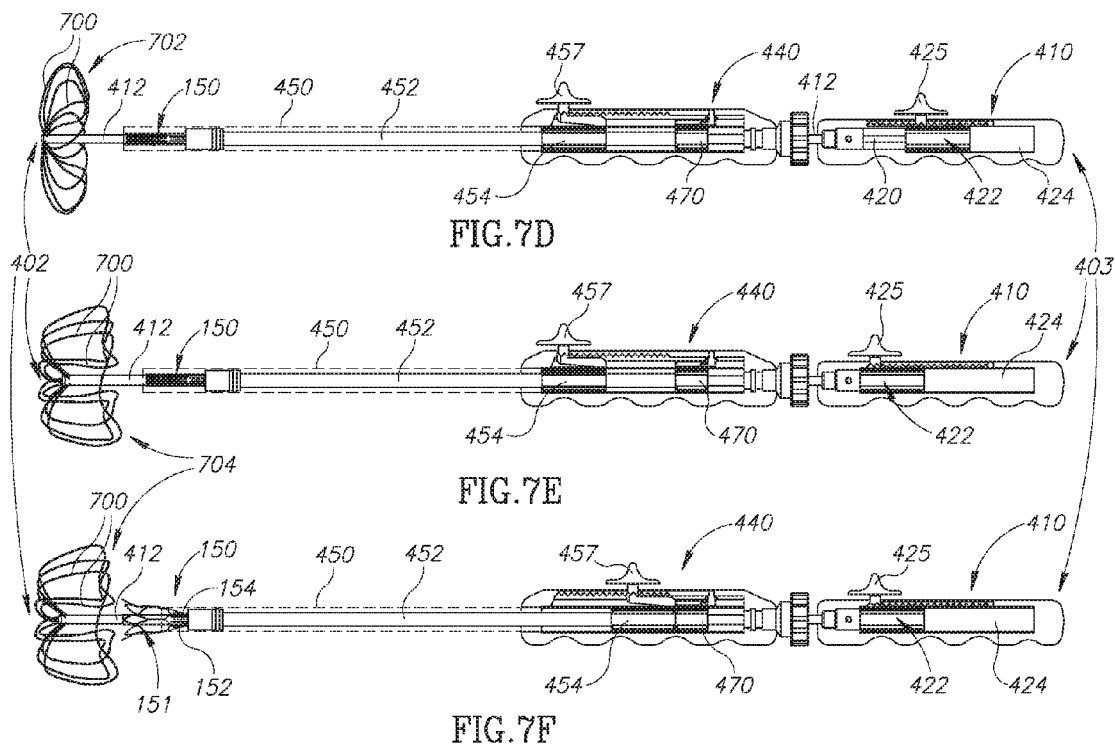

CARDIAC PROSTHESES AND THEIR DEPLOYMENT

RELATED APPLICATIONS

The present application is a US National Phase Application of PCT Application No. PCT/IB2014/065147 filed on Oct. 8, 2014 and claims the benefit under 35 U.S.C. 119(e) of U.S. Provisional Application 61/888,048 filed on Oct. 8, 2013, the disclosure of which is incorporated herein by reference.

TECHNICAL FIELD

Embodiments of the invention relate to cardiac prosthesis and delivery systems for cardiac prostheses.

BACKGROUND

The human heart, and generally all mammalian hearts, comprises two blood pumps that operate in synchrony to oxygenate and deliver oxygenated blood to the body. A first pump receives deoxygenated blood after it has coursed through blood vessels in the circulatory system to deliver oxygen and nutrients to the various parts the body, and pumps the deoxygenated blood through the lungs to be oxygenated. The second pump receives the oxygenated blood from the lungs and pumps it to flow through the blood vessels of the circulatory system and deliver oxygen and nutrients to the body parts. The two pumps are located adjacent each other in the heart and each pump comprises two chambers, an atrium that receives blood and a ventricle that pumps blood.

The first pump, which receives deoxygenated blood to be pumped to the lungs, is located on the right side of the heart and its atrium and ventricle are accordingly referred to as the right atrium and right ventricle. The second pump, which receives oxygenated blood to be pumped to the body, is located on the left side of the heart and its atrium and ventricle are referred to as the left atrium and left ventricle of the heart. The right and left atria are separated by a wall in the heart referred to as the interatrial septum and the right and left ventricles are separated by a wall in the heart referred to as the interventricular septum.

Deoxygenated blood enters the right atrium via blood vessels referred to as the superior vena cava and inferior vena cava. During a part of the heart cycle referred to as diastole the right ventricle is relaxed and the deoxygenated blood in the right atrium flows from the right atrium into the right ventricle via a valve, referred to as a tricuspid valve, which connects the right atrium to the right ventricle. The right ventricle contracts during a part of the heart cycle referred to as systole, to pump the deoxygenated blood that it receives from the right atrium out of the ventricle and into the pulmonary artery via a valve referred to as the pulmonary valve. The pulmonary valve interfaces the pulmonary artery with the right ventricle. The pulmonary artery delivers the deoxygenated blood to the lungs for oxygenation. The tricuspid and pulmonary valves control direction of blood flow in the right side of the heart. The tricuspid valve opens to let deoxygenated blood flow from the right atrium into the right ventricle and closes to prevent deoxygenated blood from regurgitating into the right atrium when the right ventricle contracts. The pulmonary valve opens to let blood enter the pulmonary artery when the right ventricle contracts and closes to prevent blood regurgitating into the right ventricle when the right ventricle relaxes to receive blood from the right atrium.

The left atrium receives oxygenated blood from the lungs via pulmonary veins. Oxygenated blood flows from the left atrium into the left ventricle during diastole via a bicuspid valve referred to as the mitral valve, which opens during diastole to allow blood flow from the left atrium to the left ventricle. The left ventricle contracts during systole to pump the oxygenated blood that it receives from the left atrium out of the heart through the aortic valve and into the aorta, for delivery to the body. The mitral valve operates to prevent regurgitation of oxygenated blood from the left ventricle to the left atrium when the left ventricle contracts to pump oxygenated blood into the aorta. The aortic valve closes to prevent blood from regurgitating into the left ventricle when the left ventricle relaxes to receive blood from the left atrium.

Each valve comprises a set of matching "flaps", also referred to as "leaflets" or "cusps". that are mounted to and extend from a supporting structure of fibrous tissue. The supporting structure has a shape reminiscent of an annulus and is often conventionally referred to as the annulus of the valve. The leaflets are configured to align and overlap each other, or coapt, along free edges of the leaflets to close the valve. The valve opens when the leaflets are pushed away from each other and their free edges part. The aortic, pulmonary, and tricuspid valves comprise three leaflets. The mitral valve comprises two leaflets.

The leaflets in a valve open and close in response to a gradient in blood pressure across the valve generated by a difference between blood pressure on opposite sides of the valve. When the gradient is negative in a "downstream flow" or antegrade direction, in which the valve is intended to enable blood flow, the leaflets are pushed apart in the downstream, antegrade direction by the pressure gradient and the valve opens. When the gradient is positive in the downstream direction, the leaflets are pushed together in the upstream or retrograde direction so that their respective edges meet to align and coapt, and the valve closes.

For example, the leaflets in the mitral valve are pushed apart during diastole to open the mitral valve and allow blood flow from the left atrium into the left ventricle when pressure in the left atrium is greater than pressure in the left ventricle. The leaflets in the mitral valve are pushed together so that their edges coapt to close the valve during systole when pressure in the left ventricle is greater than pressure in the left atrium to prevent regurgitation of blood into the left atrium.

Each valve is configured to prevent misalignment or prolapse of its leaflets as a result of positive pressure gradients pushing the leaflets upstream past a region in which the leaflets properly align and coapt to close the valve. A construction of fibrous tissue in the leaflets of the pulmonary and aortic valves operates to prevent prolapse of the leaflets in the pulmonary and aortic valves. A configuration of cord-like tendons, referred to as chordae tendineae, connected to muscular protrusions, referred to as papillary muscles, that project from the left ventricle wall tie the leaflets of the mitral valve to the walls of the left ventricle. The chordate tendinea provide dynamic anchoring of the mitral valve leaflets to the left ventricle wall that operate to limit upstream motion of the leaflets and prevent their prolapse into the left atrium during systole. Similarly, a configuration of chordae tendineae and papillary muscles cooperate to prevent prolapse of the tricuspid valve leaflets into the right atrium.

Efficient cardiac valve function can be complex and a cardiac valve may become compromised by disease or injury to an extent that warrants surgical intervention to effect its repair or replacement. For example, normal mitral valve opening and closing and prevention of regurgitation of blood from the left ventricle into the left atrium is dependent on coordinated temporal cooperation of the mitral leaflets, the mitral annulus, the chordae, papillary muscles, left ventricle, and left atrium. Malfunction of any of these components of a person's heart may lead to mitral valve dysfunction and regurgitation that warrants surgical intervention to provide the person with an acceptable state of health and quality of life.

SUMMARY

An aspect of an embodiment of the invention relates to providing a prosthetic heart valve and transcatheter method of deploying the prosthetic heart valve to replace a native heart valve. Optionally, the prosthetic heart valve is a prosthetic mitral valve (PMV) for controlling blood flow between a patient's left atrium and left ventricle.

In an embodiment of the invention the prosthetic mitral valve comprises a wire mesh configured to self expand, or be expanded by balloon, from a cylindrical collapsed state to a "cinch-girdle" expanded state having upper and lower cup-like structures, optionally referred to as "cups", joined at a relatively narrow waist. The PMV is positioned between the leaflets of the native valve it is intended to replace with the wire mesh constrained in the collapsed state, and released to expand to the expanded state, hereinafter also referred to as a deployed state, to push aside the native leaflets and replace the native valve. The narrow waist of the PMV is shaped to seat on the annulus of the native valve, with the upper and lower cups located respectively in the left atrium and left ventricle embracing the annulus.

The lower cup optionally comprises a plurality hooks which are shaped to puncture and anchor in the wall of the ventricle, optionally in a sub-annular tissue region of the left ventricle, upon expansion of the PMV to the deployed state. Optionally, the hooks are "shoulder hooks" located on the lower cup in the vicinity of the narrow waist. In an embodiment of the invention the lower cup comprises a plurality of tails each having at least one hook shaped to puncture and anchor in the wall of the ventricle. The tails are configured to splay out and drive the hooks into the ventricle wall when the PMV expands to its deployed state.

The narrow waist embracing the native mitral valve annulus and the hooks anchored to the ventricle wall operate to stabilize the position of the PMV in the heart and reduce a probability of the PMV dislodging as the heart pumps and pressure gradients across the PMV change. Prosthetic leaflets that are mounted to the wire mesh conform to the cinch-girdle form of the deployed PMV and respond to blood pressure gradients between the left atrium and left ventricle to open and close the PMV. The leaflets contoured to the hourglass shape aid in reducing paravalvular leakage of blood.

A transcatheter delivery system (TDS) for deploying a PMV in accordance with an embodiment of the invention to replace a native mitral valve of a patient's heart comprises a delivery tube having mounted to a distal end of the delivery tube a wire scaffolding configured to self expand, or be expanded by balloon from a cylindrical collapsed state to an expanded state. The expanded state of the scaffolding is designed so that the scaffolding may be positioned in the left atrium of the heart to contact walls of the atrium and atrial tissue in the region of the native valve. The PMV is mounted in its collapsed cylindrical state on the delivery tube so that, optionally, a portion of the PMV that self expands to form the upper cup of the deployed PMV is concentric with and lies over the wire scaffolding. The PMV is held fixed to the delivery tube, optionally by at least one spur comprised on the mounting tube and a PMV control tube concentric with the delivery tube. The at least one spur mates with a tail of the PMV, and the PMV control tube presses on the tail to hold the spur and tail mated and thereby the PMV fixed to the delivery tube. The PMV control tube may be translatable in a proximal direction along the delivery tube to release the PMV from the delivery tube. A control sheath concentric with the delivery tube and the PMV control tube constrains the scaffolding and the portion of the PMV overlying the scaffolding in their respective collapsed states. The control sheath may be translatable in a proximal direction to release the scaffolding and the overlying portion of the PMV so that they expand to their respective expanded states.

To deploy the PMV in accordance with an embodiment of the invention, the delivery tube is optionally apically inserted into the heart and through the native mitral valve to position the scaffolding and upper cup portion of the PMV overlying the scaffolding in their collapsed states in the atrium. The control sheath is then translated to release the scaffolding and overlying upper cup portion of the PMV so that the scaffolding expands to contact the left atrium wall and the overlying portion of the PMV expands to form the upper cup of the PMV and cup the scaffolding. The PMV control tube on the other hand remains positioned to lock the tails of the lower cup to the delivery tube and constrain the portion of the PMV that expands to form the lower cup in the collapsed state and maintain the PMV in a partially expanded state. In the partially expanded state, with the lower cup of the PMV collapsed and locked to the delivery tube, the delivery tube may be maneuvered to adjust position the PMV so that it is advantageously located before being opened and fully deployed to replace the native mitral valve. Adjustment of the position of the PMV is facilitated by the expanded scaffolding, which by contacting the atrium wall and atrial tissue in the vicinity of the mitral valve moderates motion of the atrium and the native mitral valve relative to the PMV.

Upon properly positioning the half opened PMV at the native mitral valve, the PMV control tube is translated to release the collapsed lower cup of the PMV to assume its expanded cup shape and enable the PMV tails splay open and drive and anchor their hooks into the ventricle wall. Optionally, the hook of a PMV tail is driven into the ventricle wall at the submitral annular position or in the mid or apical part of the ventricle walls. With expansion of the lower cup and the hooks anchored in the ventricle wall the PMV is fully deployed, anchored to the left ventricle with its cinch-girdle form seated on and embracing the native mitral valve annulus. Following deployment, the control sheath is translated along the delivery tube toward the distal end of the tube to collapse the scaffolding. The delivery tube and collapsed scaffolding are then withdrawn and removed from the heart.

According to an embodiment of the invention a TDS, hereinafter also referred to as an independent action TDS (IA-TDS) may comprise a scaffolding in a collapsed state and a PMV in a collapsed state that may not overlie the scaffolding. The scaffolding may be constrained between inner and outer scaffolding control tubes and the PMV may be constrained between inner and outer PMV control tubes. The scaffolding and PMV control tubes are controllable to position and release the scaffolding and PMV from their collapsed states to their respective expanded states independent of each other. In an embodiment of the invention the scaffolding may be housed in an outer control tube, hereinafter also referred to as a scaffolding deployment tube, and a push control rod mounted inside the outer control tube may be used to push the scaffolding out of the outer control tube to deploy the scaffolding.

In an embodiment of the invention, a PMV, hereinafter referred to as a "crown PMV", deployed by an IA-TDS in accordance with an embodiment of the invention may comprise a wire mesh having a shape reminiscent of a crown. The crown PMV may be formed having tails that splay out to drive anchor hooks into the ventricle wall of a heart into which the PMV is deployed. Optionally, the crown PMV comprises leaflet support struts to which portions of leaflets of the PMV are mounted. Whereas a crown PMV in accordance with an embodiment of the invention is described as deployed using an IA-TDS, a crown PMV may be deployed by any suitable TDS, such as, by way of example, the TDS described with reference to the "hourglass PMV".

In the discussion, unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the description and claims is considered to be the inclusive "or" rather than the exclusive or, and indicates at least one of, or any combination of items it conjoins.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical features that appear in more than one figure are generally labeled with a same label in all the figures in which they appear. A label labeling an icon representing a given feature of an embodiment of the invention in a figure may be used to reference the given feature. Dimensions of features shown in the figures are chosen for convenience and clarity of presentation and are not necessarily shown to scale.

FIGS. 7B-7H schematically show different operating states of the IA-TDS shown in FIG. 7A, in accordance with an embodiment of the invention;

DETAILED DESCRIPTION

Figure 1:
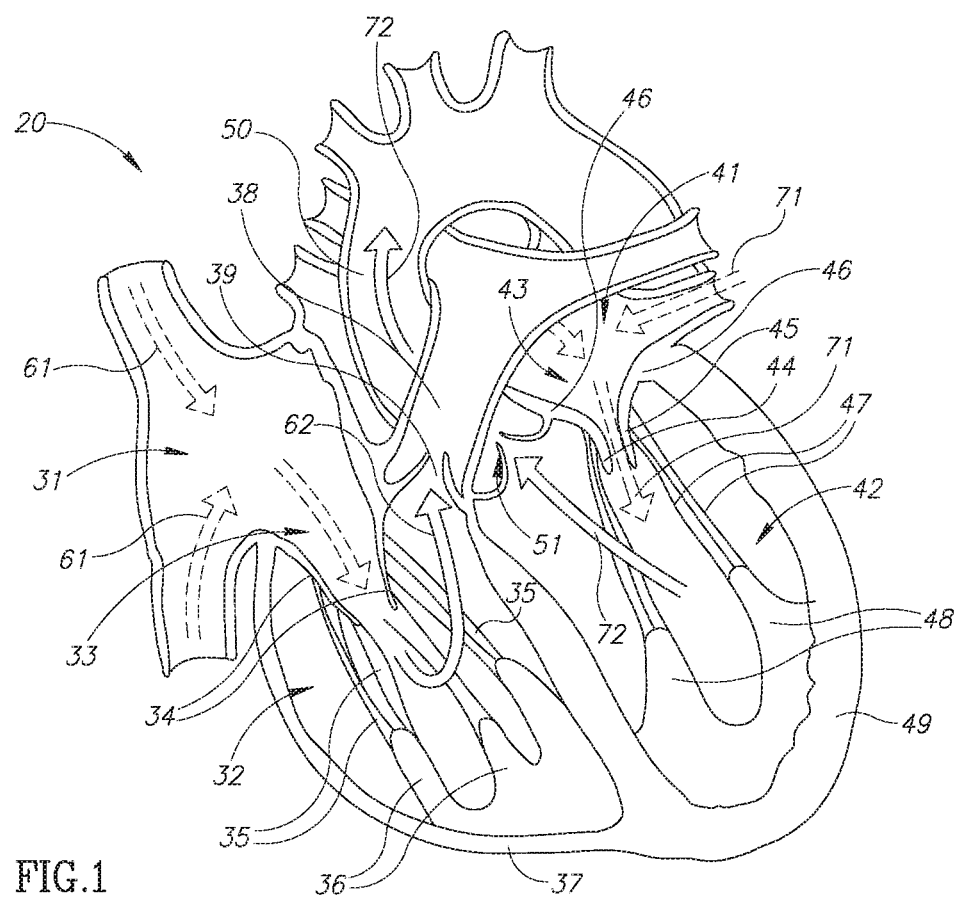
FIG. 1 schematically shows a cross section of a human heart that displays the heart chambers and cardiac valves.

FIG. 1 shows a schematic, stylized cross section of a human heart 20 having a right atrium 31 and a right ventricle 32 that communicate via a tricuspid valve 33 and a left atrium 41 and left ventricle 42 that communicate via a mitral valve 43. Tricuspid valve 33 has three leaflets 34, only two of which are shown in FIG. 1, that are tied by chordae tendineae 35 and papillary muscles 36 to the wall 37 of the right ventricle. Right ventricle 32 communicates with the pulmonary artery 38 via the pulmonary valve 39. Mitral valve 43 has two leaflets, anterior and posterior leaflets 44 (anterior leaflet 44 is in continuity with the wall of the aorta) and 45 respectively that are supported and extend from the mitral annulus 46. Mitral valve leaflets 44 and 45 are respectively tied by chordae tendineae 47 and papillary muscles 48 to the ventricle wall 49. The left ventricle communicates with the aorta 50 via the aortic valve 51.

Deoxygenated blood returning from parts of the body enters right atrium 31 and passes through tricuspid valve 33 to enter right ventricle 32 during diastole when leaflets 34 of the tricuspid valve 33 are separated (as schematically shown n FIG. 1 to open the tricuspid valve and the right ventricle relaxed. Flow of deoxygenated blood into the right atrium and through tricuspid valve 33 into the right ventricle is schematically indicated by dashed line block arrows 61. During systole right ventricle 32 contracts to pump the deoxygenated blood through pulmonary valve 38 and into the pulmonary artery 39 for delivery to the lungs. During systole leaflets 34 of tricuspid valve 33 coapt and the tricuspid valve 33 closes to prevent deoxygenated blood pumped by the right ventricle from regurgitating into the right atrium. Flow of deoxygenated blood pumped by right ventricle 32 into pulmonary artery 39 is schematically indicated by solid line block arrows 62.

Oxygenated blood from the lungs enters left atrium 41 and passes through mitral valve 43 to enter left ventricle 42 during diastole when leaflets 44 and 45 are separated (as shown in FIG. 1) to open the mitral valve and the left ventricle is relaxed. Flow of oxygenated blood into the left atrium and through mitral valve 33 into the left ventricle is schematically indicated by dashed block arrows 71. During systole left ventricle 32 contracts to pump the oxygenated blood through the aortic valve 51 and into the aorta 50 for delivery to the body. During systole leaflets 44 and 45 coapt to close mitral valve 43 and prevent oxygenated blood pumped by the left ventricle from regurgitating into the left atrium.

Valves 33, 39, 43, and 51 operate to direct flow of blood in the heart and out from the heart and their proper and efficient function are required to maintain a person's health and quality of life. Various different disease processes may result in damage to a heart valve and compromise valve functioning. For example, functioning of the mitral valve may be compromised by various degrees of stenosis, calcification, distortion of the mitral valve annulus, torn chordae tendineae, and faulty left ventricle functioning. Valve dysfunction and concomitant regurgitation may become so severe as to warrant surgical intervention to provide a person with an acceptable state of health and quality of life.

Figure 2A:
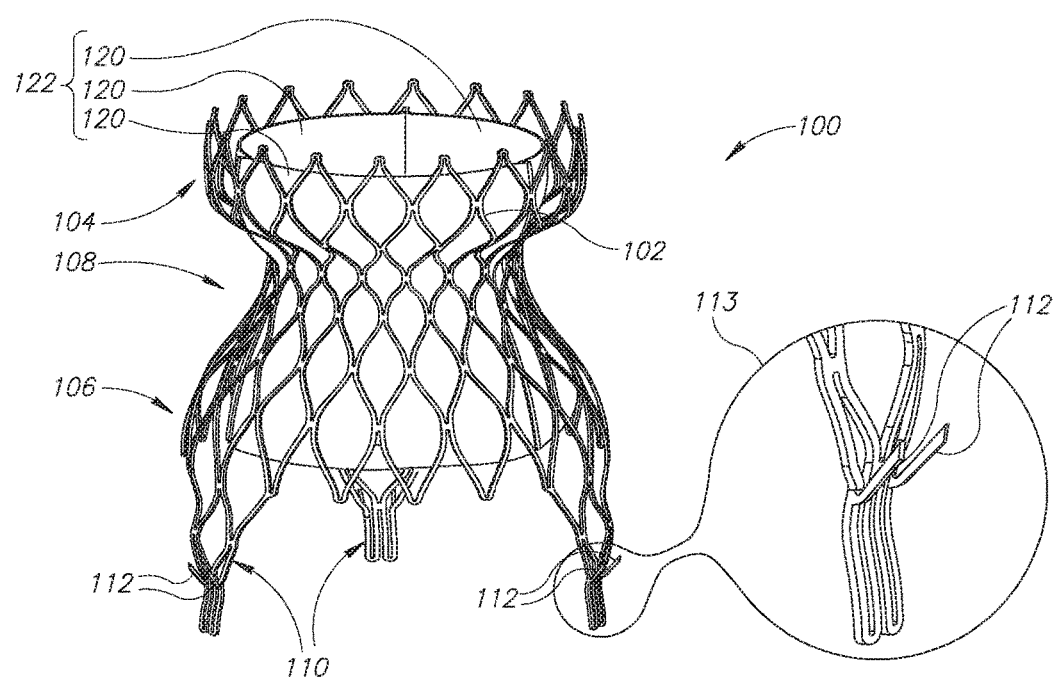
FIG. 2A schematically shows a PMV in accordance with an embodiment of the invention.

FIG. 2A schematically shows a PMV 100 that self expands when not constrained from a cylindrical collapsed shape to a cinch-waist expanded shape, which may be used to replace a native mitral valve, in accordance with an embodiment of the invention. PMV 100, which is shown in its expanded state in FIG. 2A, is delivered to a site of a native mitral valve that it is to replace in the collapsed state. Delivery and deployment of PMV 100 to the location of the native mitral valve it replaces and a transcatheter delivery system for effecting the delivery are discussed below with reference to FIGS. 3A-3F.

PMV 100 comprises a cinch-girdle wire mesh 102 having an upper cup 104 and a lower cup 106 connected by a narrow waist region 108. Upper cup 104 is configured to be positioned in the left atrium. Lower cup 106 is configured to be positioned in the left ventricle and comprises, optionally, a plurality of three tails 110 each having optionally two hooks 112 for anchoring PMV to the wall of the left ventricle. An inset 113 shows a portion of a tail 110 and hooks 112 that it comprises greatly enlarged for convenience of viewing. Narrow waist 108 is configured to seat on the annulus of the native mitral valve that the PMV replaces with upper and lower cups embracing the annulus. A plurality of optionally three artificial leaflets 120 that operate to open and close PMV 100 are sewn to wire mesh 102 and optionally form part of a skirt 122 that follows the cinch-waist contour of wire mesh 102.

Figure 2B:
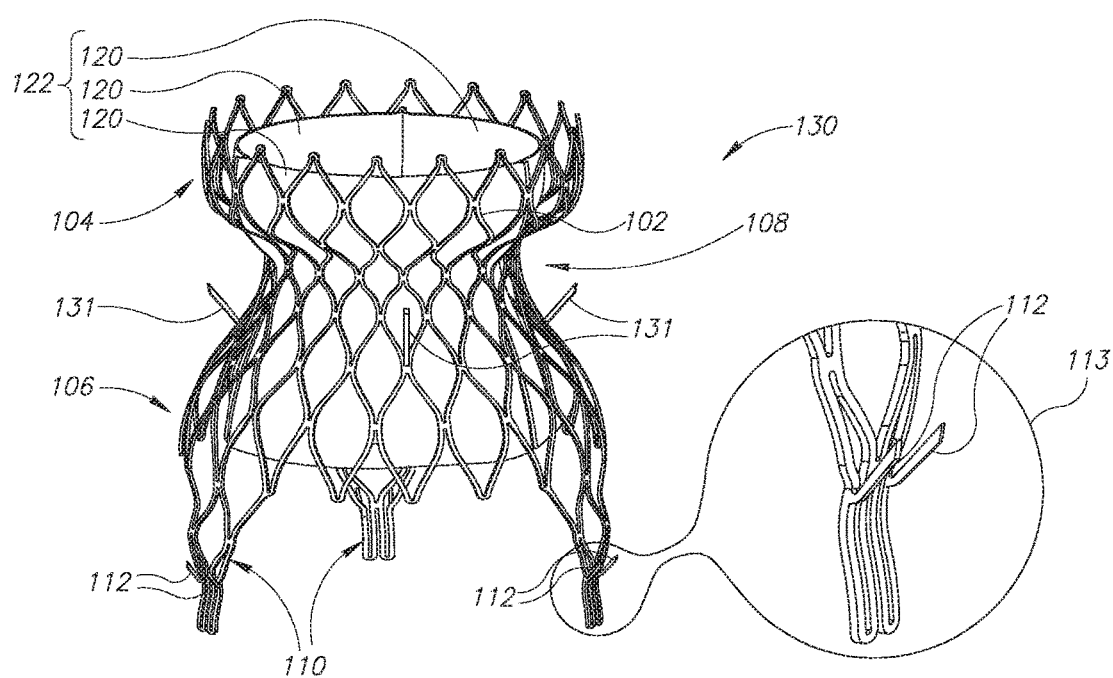
FIGS. 2B-2C schematically show variations of the PMV shown in FIG. 2A.
Figure 2C:
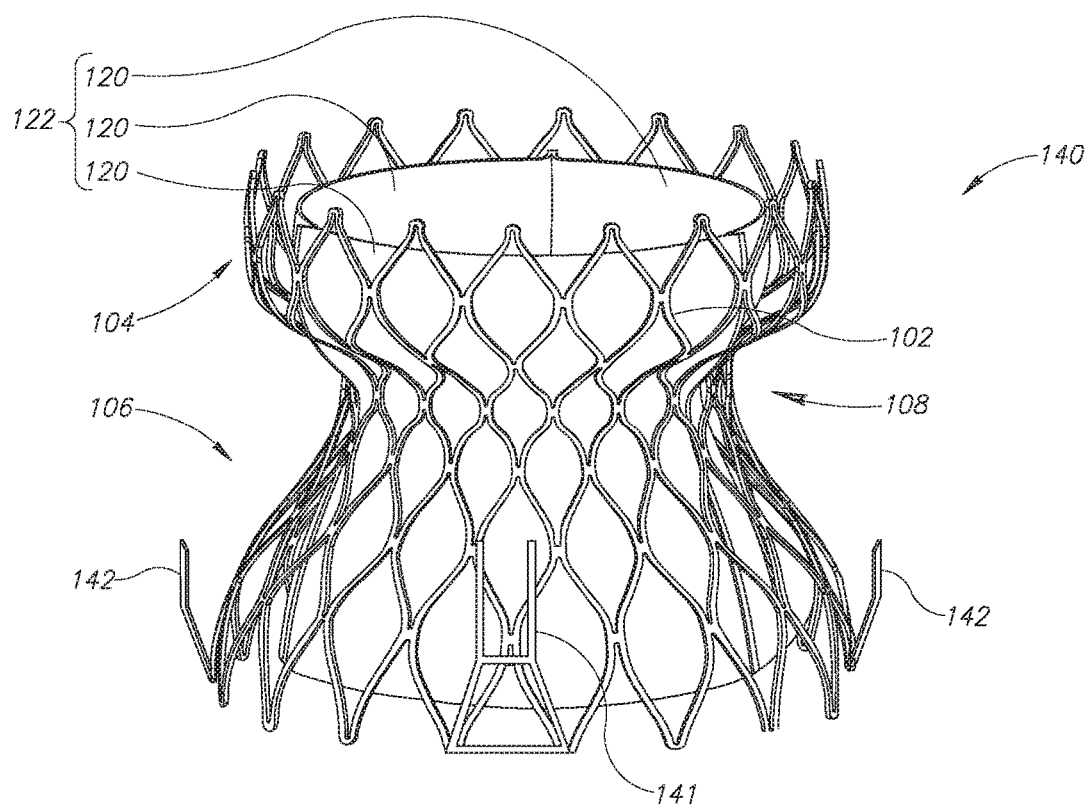

FIGS. 2B-2C schematically show variations of the PMV 100, in accordance with an embodiment of the invention. FIG. 2B schematically shows a PMV 130, which optionally is identical or similar to PMV 100 except for comprising "shoulder" hooks 131 located on lower cup 106. Shoulder hooks 131 fold out from wire mesh 102 when PMV 130 expands from a collapsed state to an expanded state and are configured to penetrate and anchor to sub-annular tissue in left ventricle 42 (FIGS. 1, 2D), on the underside of annulus 46 or just below mitral annulus 46 (FIGS. 1, 2D) along wall 49 of the ventricle. FIG. 2C schematically show a PMV 140 that is optionally identical or similar to PMV 100 but comprises "everting hooks" 142 which fold back from or fold out from wire mesh 102 when PMV 140 expands from a collapsed state to an expanded state. Everting hooks 142 are configured to anchor PMV 140 to a sub-annular tissue region in ventricle 42, on the underside of annulus 46 or just below the annulus along wall 49 of the ventricle.

Figure 2D:
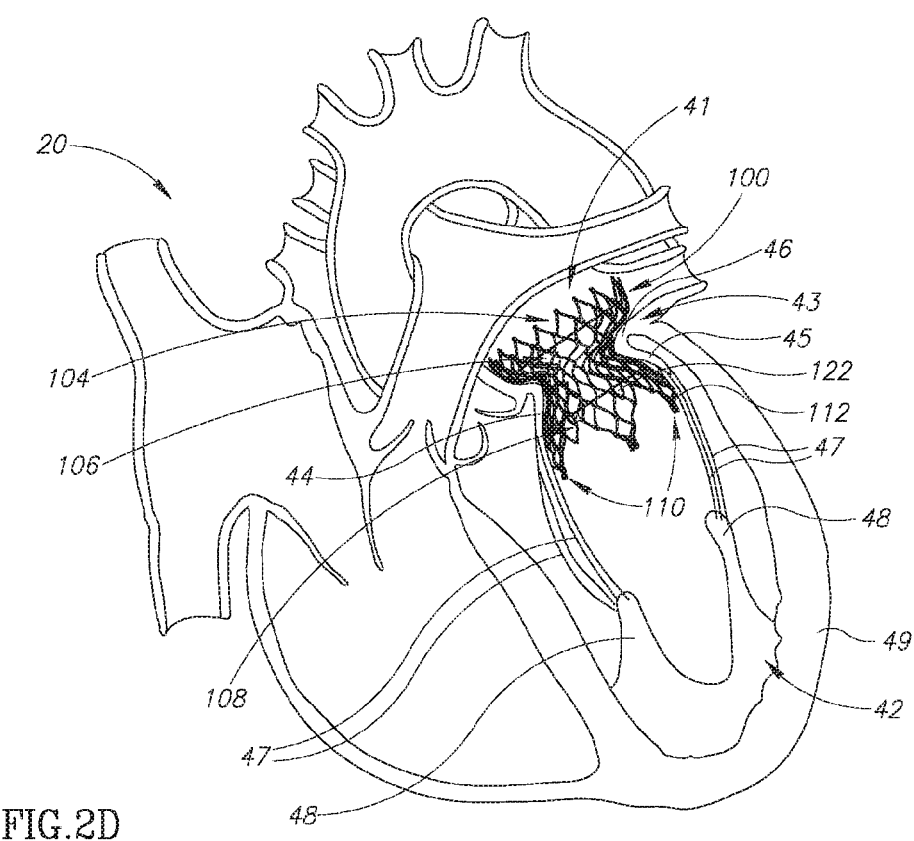
FIG. 2D schematically shows the PMV shown in FIG. 2A deployed in a heart, in accordance with an embodiment of the invention.

FIG. 2D schematically shows PMV 100 deployed to replace native mitral valve 43 of schematic heart 20 shown in FIG. 2A. When deployed, PMV 100 pushes native leaflets 44 and 45 aside towards wall 49 of ventricle 42, and waist region 108 of the PMV seats on annulus 46 of native mitral valve 43. Upper and lower cups 104 and 106 of PMV embrace annulus 46 from the atrial side of annulus 46 and the ventricle side of annulus 46 respectively, and hooks 112 puncture and anchor into the wall 49 of ventricle 42. The anchoring of hooks 112 in wall 49 of ventricle 42 and the embrace of annulus 46 by upper and lower cups 104 and 106 provide a robust anchor of PMV 100 in place of native mitral valve 43 between atrium 41 and ventricle 42. Leaflet skirt 122 conforming to the cinch-waist contour of PMV 100 operates to seal PMV 100 to annulus 46 and reduce probability of paravalvular leakage of blood around the PMV.

It is noted that whereas when properly deployed, all hooks 112 comprised in PMV 100 are anchored in ventricle wall 49, FIG. 2D, shows only one tail 110 and hook 112 belonging to the tail in contact with ventricle wall 49 because the cross section view provided by the figure does not readily provide the three dimensional image required to show all hooks 112 properly anchored in ventricle wall 49.

Figure 3A:
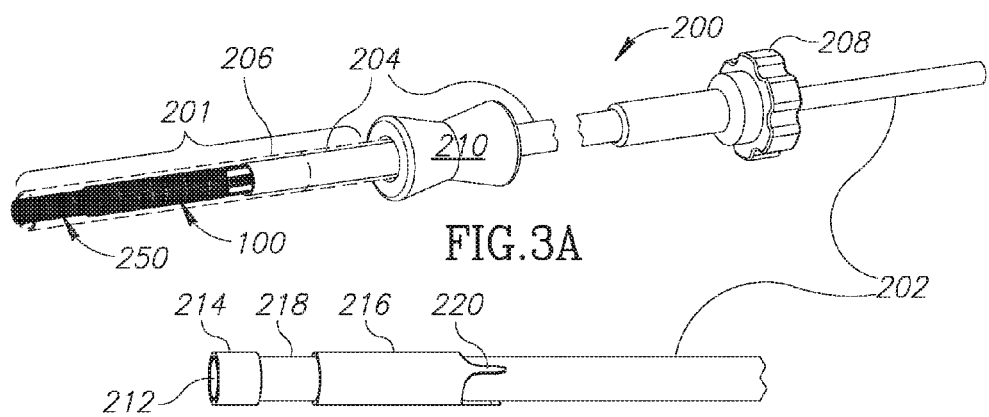
FIGS. 3A-3F schematically show components of a TDS and relationships of the components, in accordance with an embodiment of the invention.

FIG. 3A schematically shows a transcatheter delivery system (TDS) 200 for delivering and deploying a prosthetic cardiac valve, such as PMV 100 shown in FIGS. 2A and 2D, in accordance with an embodiment of the invention. FIGS. 3B-3F schematically show enlarged images of features and components of PMV 100 and TDS 200 comprised in a distal portion 201 of TDS 200. Distal portion 201 is positioned in the heart at the site of a native mitral valve being replaced by PMV 100 when using TDS 200 to deploy PMV 100 to replace the native mitral valve. Operation of TDS 200 is discussed below with reference to FIGS. 4A-4E and a transapical mitral valve replacement (TAMVR) procedure for deploying PMV 200 using TDS 200 is schematically illustrated in FIGS. 5A-5D and discussed with reference to the figures.

Referring to FIG. 3A, TDS 200 optionally comprises a delivery tube 202 and, a PMV control tube 204 and a control sheath 206 concentrically mounted to the delivery tube. PMV control tube 204 is translatable along delivery tube 202 and may be locked to the delivery tube at locations along the length of the delivery tube by rotating a knob 208 to which the PMV control tube is connected. Control sheath 206 is coupled to a draw handle 210 and may be moved back and forth along PMV control tube 204 by translating draw handle 210 along the PMV control tube. Optionally, draw handle 210 "hugs" PMV control tube 204 so that whereas control sheath 206 may be relatively easily moved along PMV control tube 204, friction between the draw handle and the PMV control tube is generally sufficient to prevent its displacement along the PMV control tube without manual operation of the draw handle.

Figure 3B:
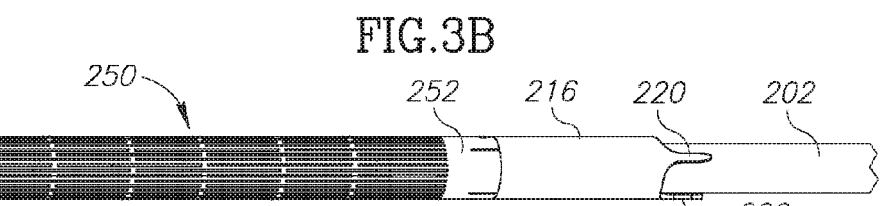
Figure 3C:
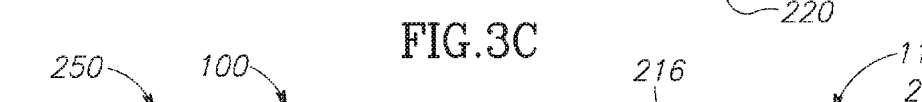
Figure 3D:
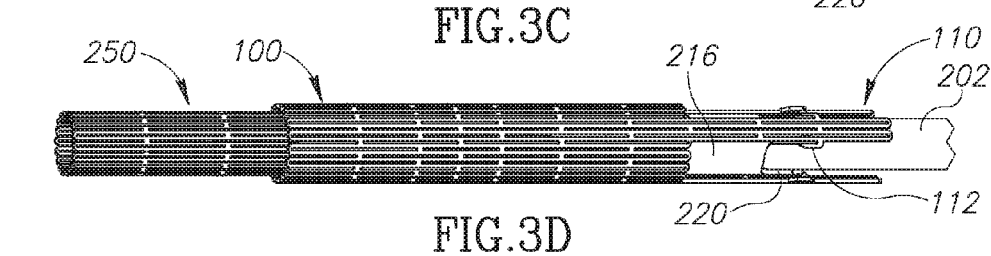
Figure 3E:
Figure 3F:
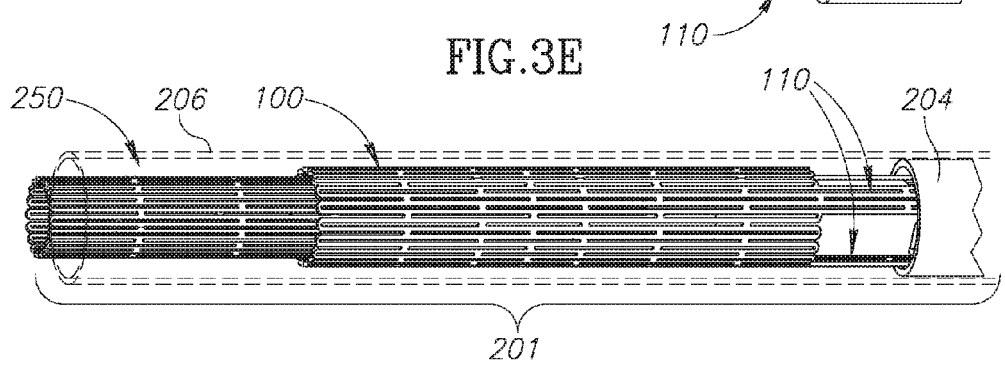

An optionally self-expanding wire scaffolding 250 in a cylindrical collapsed state is connected at a distal end 212 (FIG. 3B) of delivery tube 202. Optionally, a PMV 100 is mounted in its collapsed cylindrical state to delivery tube 202 so that a portion of the PMV that expands to form upper cup 104 (FIG. 2A) overlaps a portion of scaffolding 250. Control sheath 206, when it surrounds wire scaffolding 250 and PMV 100, as shown in FIG. 3A, and FIG. 3F discussed below, prevents their release and expansion away from their respective collapsed states.

Scaffolding 250 is optionally rotatably secured to distal end 212 of delivery tube 202 by an end ring 214 and a tube collar 216 displaced from the end ring at the distal end of delivery tube 202. End ring 214 and tube collar 216 are schematically shown in FIG. 3B. Displacement of tube collar 216 from end ring 214 forms an annular recess 218 surrounding delivery tube 202 between the end ring and the tube collar. In an embodiment of the invention, as schematically shown in FIG. 3C scaffolding 250 comprises a scaffolding collar 252, which is captured in annular recess 218 between end ring 214 and tube collar 216 to mount scaffolding 250 to distal end 212 of delivery tube 202. Scaffolding collar 250 has an inner diameter smaller than an outer diameter of either end ring 214 or tube collar 216 but sufficiently larger than an outer diameter of delivery tube 202 to allow scaffolding 250 to rotate about an axis (not shown) of the delivery tube.

Tube ring 216 comprises at least one spur 220 that is used to secure PMV 100 to delivery tube 202. In an embodiment of the invention, PMV 100 is mounted to delivery tube 202 so that a portion of the PMV, as shown in FIG. 3D, overlays scaffolding 250, and each tail 110 comprising hooks 112 sits on a spur 220. PMV control tube 204 overlays and presses together tails 110 and the spurs 220 that they respectively lie on so that as long as the PMV control tube 204 lies and presses on the tails, PMV 100 is held to delivery tube 202 so that it does not translate or rotate with respect to the delivery tube. When "locking" tails 110 to spurs 220, control tube 204 also prevents the lower portion of PMV 100 from expanding to an expanded state when control sheath 206 is translated towards the proximal end of delivery tube 202 to release scaffolding 250 and the portion of PMV overlying the scaffolding to expand to their respective expanded states. FIG. 3E schematically shows PMV control tube 204 lying and pressing on tails 110 of PMV 100. FIG. 3F shows an enlarged schematic image of the distal portion 201 of TDS 200 in which control sheath 206 constrains scaffolding 250 and PMV 100 to their collapsed states.

Hereinafter, positions of control sheath 206 and PMV control tube 204 in which they are constraining scaffolding 250 and/or PMV 100 or portions thereof may be referred to as "constraining positions". Positions to which the control shaft and/or the PMV control tube are moved to release scaffolding 250 and/or PMV 100 or portions thereof may be referred to as "releasing positions".

FIGS. 4A-4E schematically show operation of TDS 200's control sheath 206 and PMV control tube 204 to release scaffolding 250 and PMV 100 to expand from their collapsed to their expanded states and to return the scaffolding and PMV to their collapsed states, in accordance with an embodiment of the invention. In FIGS. 4A-4E and figures that follow, for convenience of presentation, leaflets 120 shown in FIG. 2A that operate to open and close PMV 100 are not shown.

Figure 4A:
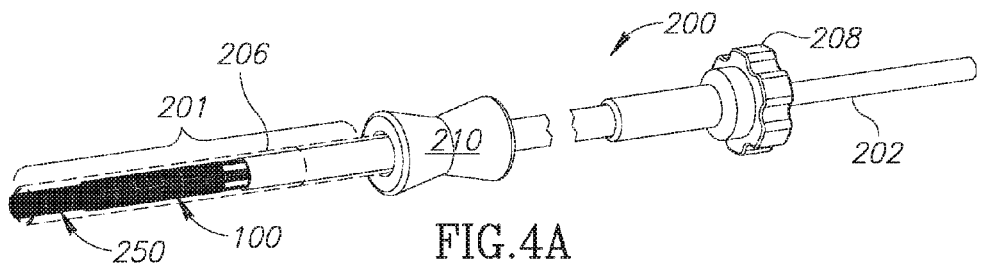
FIGS. 4A-4E schematically show operating states of the TDS shown in FIGS. 2A-2F, in accordance with an embodiment of the invention.

FIG. 4A is identical to FIG. 3A and schematically shows TDS 200 in which PMV control tube 204 is locked in a restraining position along delivery tube 202 by locking knob 208, and control sheath 206 is in a restraining position along PMV control tube 204. As a result, scaffolding 250 and PMV 100 comprised in distal portion 201 of TDS 200 are in collapsed states. In a transapical mitral valve replacement, TAMVR, procedure in accordance with an embodiment of the invention discussed below with reference to FIGS. 5A-5D, distal portion 201 of TDS 200 is introduced into the heart and positioned at the site of the mitral valve being replaced in a state, hereinafter a "delivery state", similar to that shown in FIG. 4A.

Figure 4B:
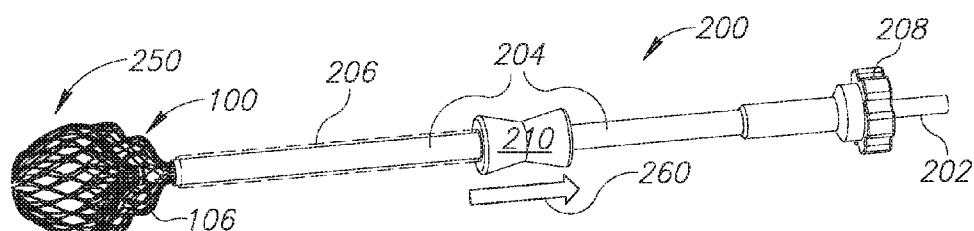

In FIG. 4B, PMV control tube 204 remains locked in the constraining position shown in FIG. 4A and draw handle 210 is manually translated in a proximal direction indicated by a block arrow 260 to move control sheath 206 along PMV control tube 204 to a releasing position. Translation of control sheath 206 to the releasing position releases scaffolding 250 to expand from its collapsed state in FIG. 4A to its expanded state, in which it assumes a relatively large ball-like volume. The restraining position of PMV control tube 204 prevents PMV 100 from expanding completely to an expanded state as a result of translation of control sheath 206, and the PMV is partially expanded in FIG. 4B. When partially expanded, portions of PMV 100 that form upper cup 104 and waist 106 (see for example, FIG. 4C) expand while a portion that expands to form lower cup 108 (FIG. 4C) remains collapsed.

In the TAMVR procedure discussed below, fully expanded scaffolding 250 is used to fill and contact the wall of the left atrium and stabilize location of TDS 200 relative to the native mitral valve being replaced to facilitate proper positioning of PMV 100 before the PMV is deployed in its fully expanded state.

Figure 4C:
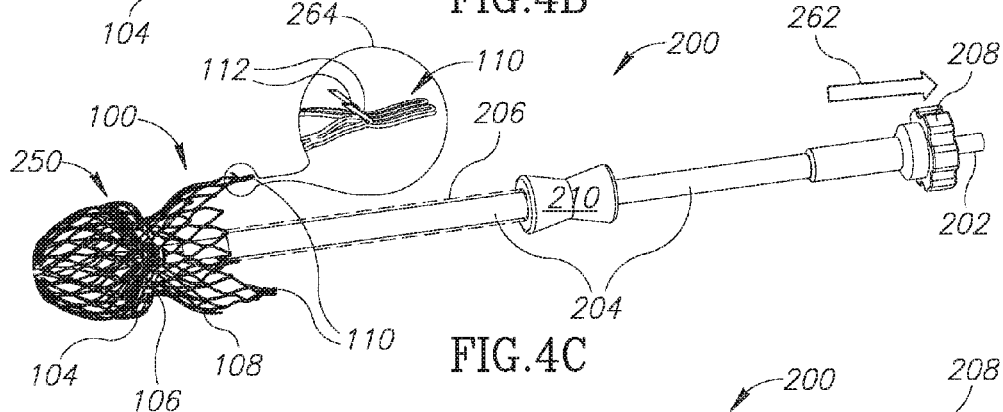

In FIG. 4C locking knob 208 is rotated to unlock PMV control tube 204 from delivery tube 202 and the locking knob and PMV control tube, and with them control sheath 206, are translated in a proximal direction indicated by block arrow 262 to a releasing position. Translation of PMV control tube 204 to a releasing position completely releases PMV 100 to fully expand to its expansion state. In the fully expanded state, PMV 100 takes on its fully deployed cinchwaist form, with upper and lower cups 104 and 108 joined by a relatively narrow waist 106 (FIGS. 2A and 2D) and tails 110 splayed out and hooks 112 raised for anchoring into the wall of a ventricle, as shown in FIGS. 2A and 2D and discussed below. Inset 264 shows an enlarged image of hooks 112.

Figure 4D:
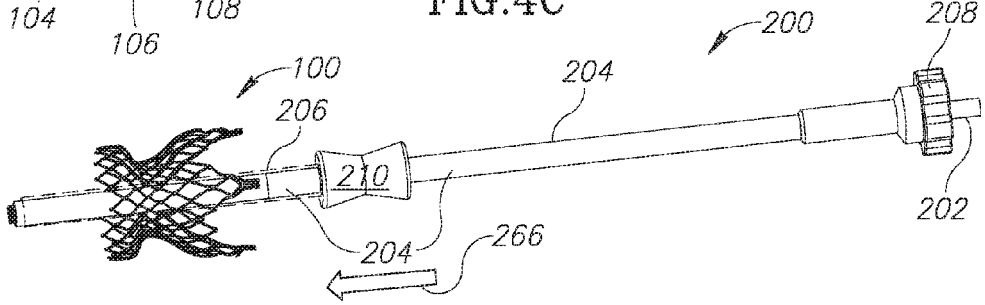
Figure 4E:
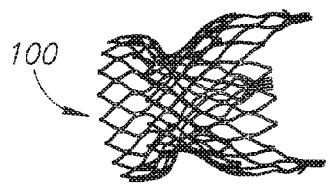

Once PMV 100 is in a fully deployed state, draw handle 210 may be translated in a distal direction indicated by a block arrow as shown in FIG. 4D, to encompass and collapse scaffolding 250 back to its collapsed state. Once returned to its collapsed state TDS 200 may be removed from PMV 100 and the heart to leave only deployed PMV 100 replacing the native mitral valve. FIG. 4E schematically shows PMV 100 after TDS 200 has been removed.

Figure 5A:
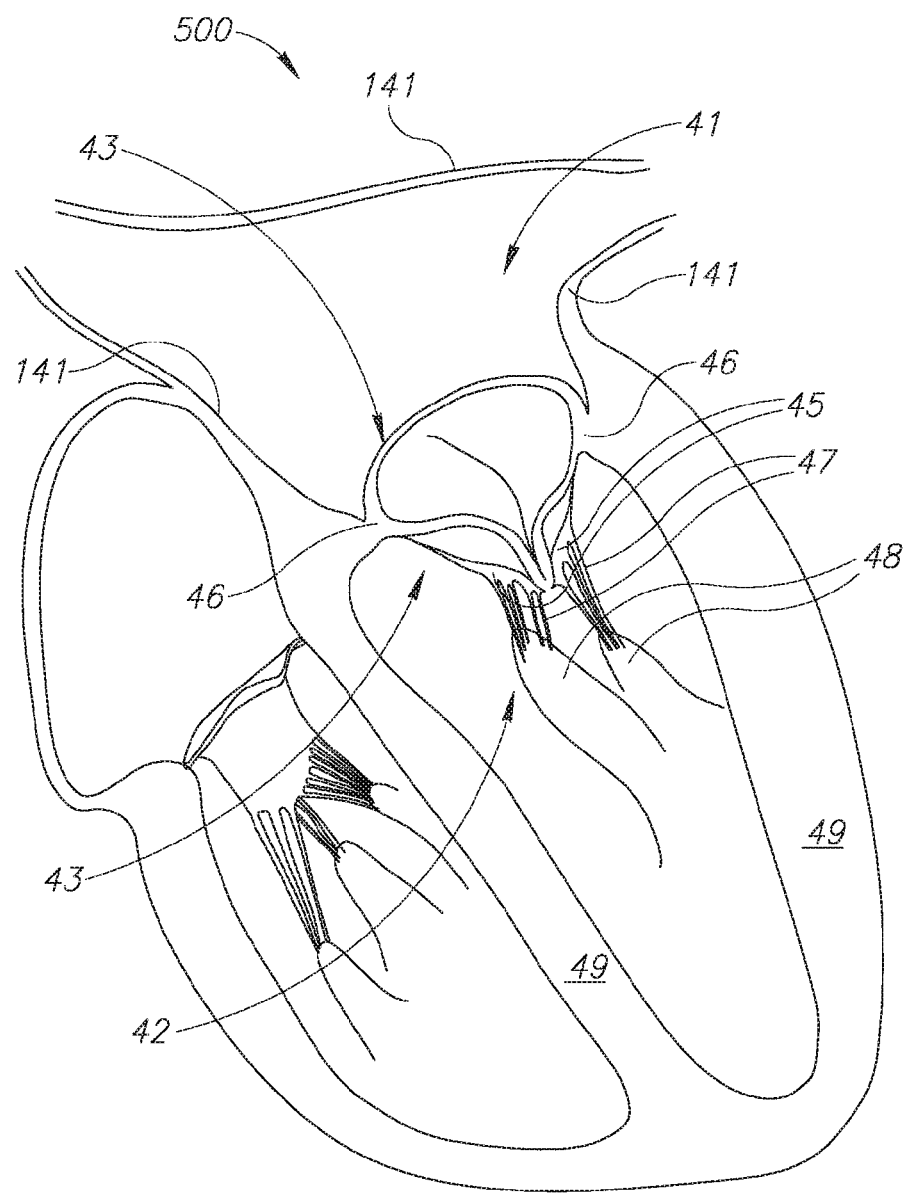
FIGS. 5A-5F schematically illustrate use of the TDS to deploy a PMV in a heart, in accordance with an embodiment of the invention.

FIG. 5A schematically shows cutaway image of a heart 500 having a native mitral valve 43 between the left atrium 41 and left ventricle 42 that is to be replaced by PMV 100 in a TAMVR procedure in accordance with an embodiment of the invention. Left atrium has a wall 141 and left ventricle 42 has wall 49. Mitral valve 43 comprises an annulus 46 that support and from which anterior and posterior leaflets 44 and 45 extend. The leaflets are anchored to ventricle wall 49 by papillary muscles 48 and chordae tendineae 47.

Figure 5B:
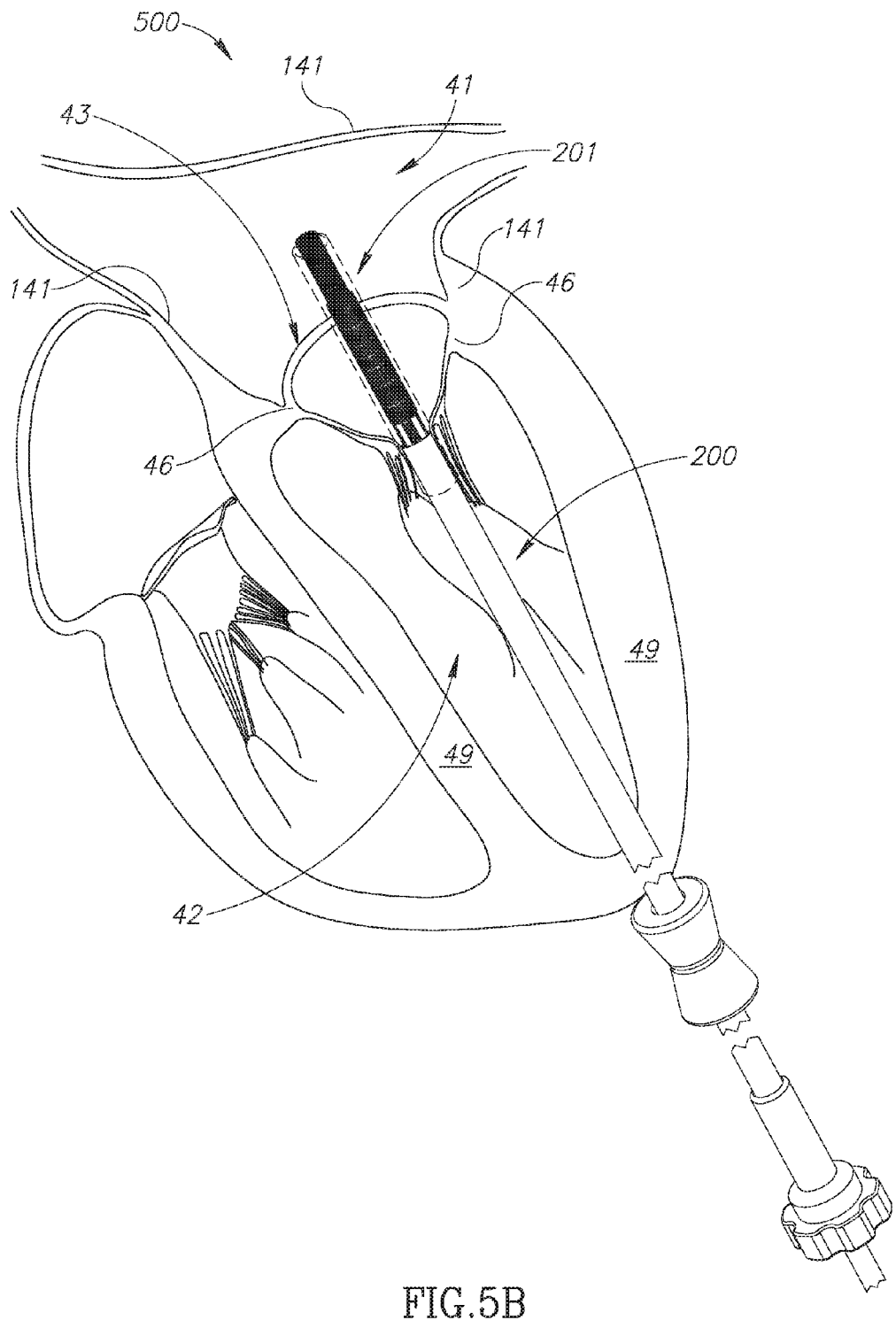

FIG. 5B schematically shows TDS 200 at the beginning of the TAMVR procedure after it has been introduced into the heart by puncturing the apex of the heart and been positioned so that a distal portion 201 of TDS 200 has passed through native mitral valve 43 to be positioned in left atrium 41. The heart may be punctured and TDS 200 positioned in the left atrium using any of well established procedures known in the art.

Figure 5C:
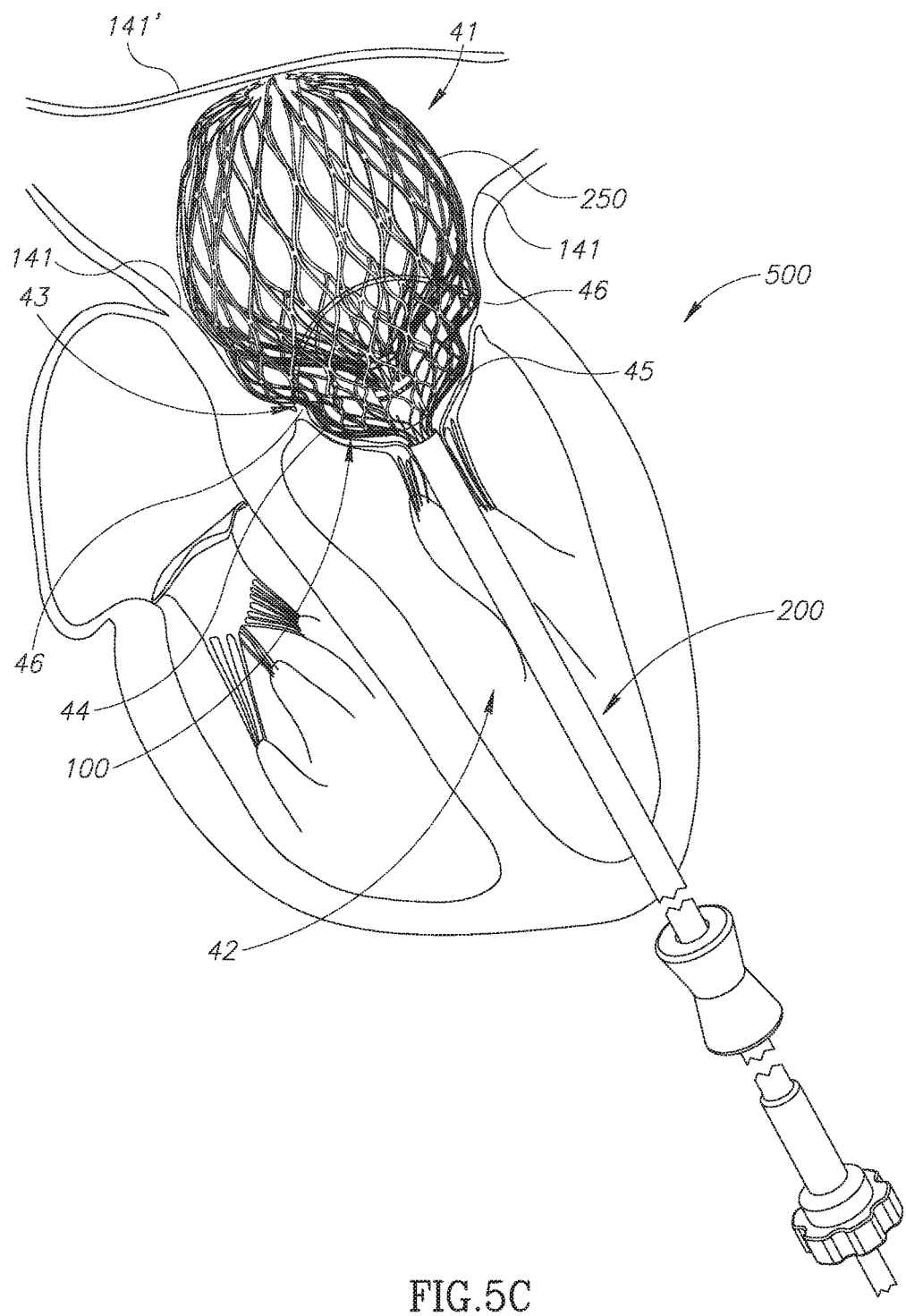

In FIG. 5C scaffolding 250 is expanded and PMV 100 is partially expanded by operating TDS 200 as discussed above with reference to FIG. 4B. With 250 expanded and PMV 100 partially expanded, PMV 100 may be oriented by rotating and/or tilting the TDS to a desired position advantageous for expanding PMV 100 to a deployed state replacing native mitral valve 43. Expanded 250 facilitates orienting PMV 100 during the TAMVR procedure, in accordance with an embodiment of the invention, by stabilizing operation and motion of native mitral valve 43 relative to TDS 200 and, optionally contributing to improved functioning of the mitral valve.

In an embodiment of the invention, scaffolding 250 is designed so that in its expanded state, as schematically shown in FIG. 5C, it contacts tissue in the vicinity of native mitral valve 43 and walls 141 of atrium 41, including a top wall 141 (FIGS. 5A, 5B) of the atrium also distinguished for clarity by the label 141'. Scaffolding 250 may be designed to assume in its expanded state any of various shapes advantageous for adapting the scaffolding to the particular shape of atrium 41 or performing a desired stabilizing or function. For example, the expanded state of scaffolding 250 may be substantially spherical, mushroom shaped, or elliptically shaped or assume a shape that is not rotationally symmetric. The scaffolding may contribute to improved functioning of the mitral valve, for example by limiting motion of native leaflets 44 and 45 and as a result their possible prolapse into left atrium 41, or by applying force to annulus 46 of the mitral valve that alters shape or functioning of the annulus that improves leaflet coaptation.

Scaffolding 250 may be made from any suitable material that may be self expanding or conveniently expanded using any of various balloon expansion technologies known in the art. For example, scaffolding 250 may be formed from a shape memory alloy such as nitinol. Scaffolding 250 may be flexible when expanded and/or sufficiently rigid to generate changes in the shape of left atrium 41 or annulus 46 of native mitral valve 43 when deployed in atrium 41.

Figure 5D:
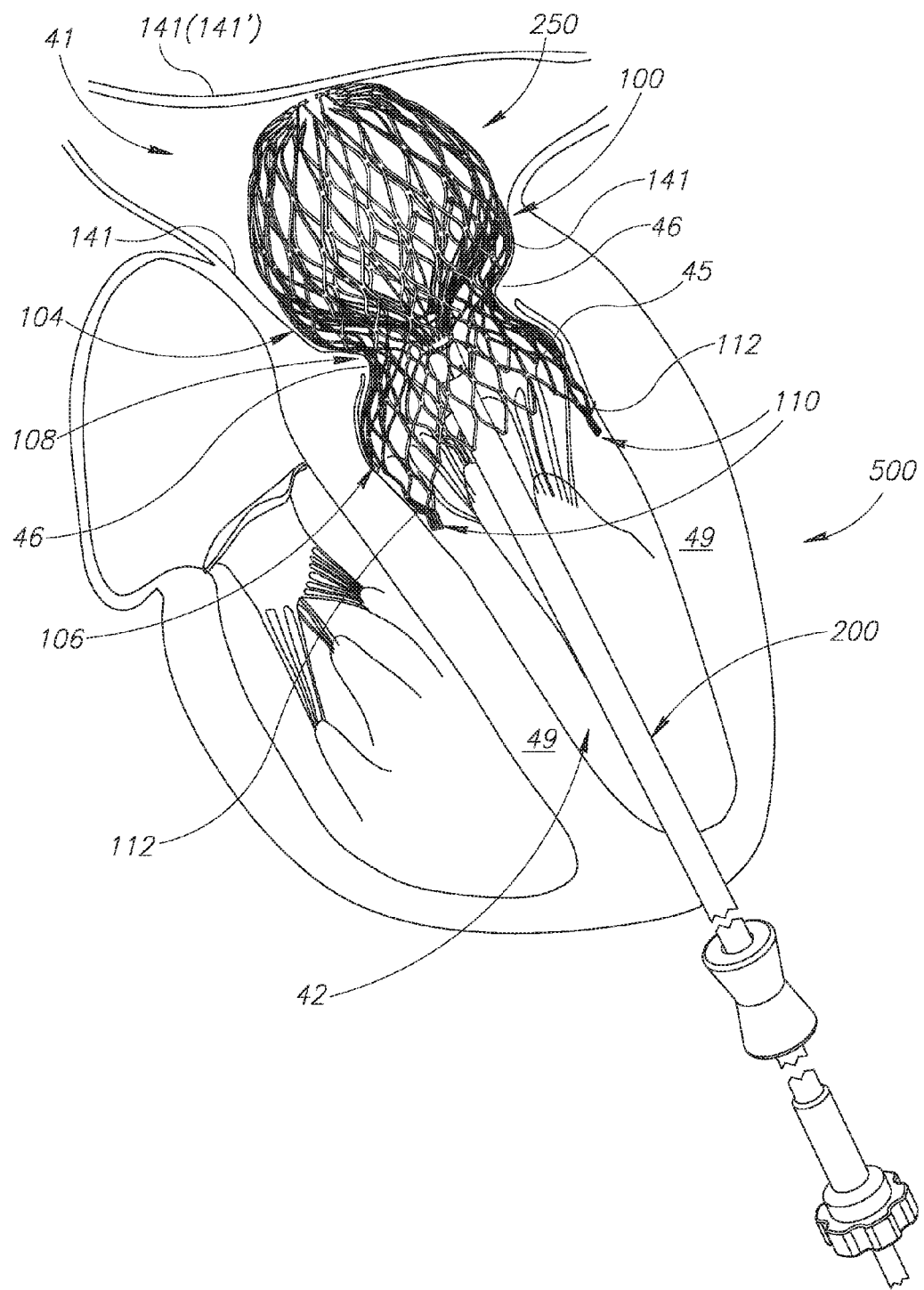

In FIG. 5D after PMV 100 is partially expanded as shown in FIG. 5C, TDS 200 is operated as discussed above with reference to FIG. 4C to fully expand PMV 100 to its cinch-waist deployed shape. In the fully expanded state upper and lower cups 104 and 106 of PMV 100 embrace annulus 46 of native mitral valve 43, and hooks 112 are anchored in wall 49 of ventricle 42. Optionally PMV 100 comprises at least one shoulder hook 131 and/or at least one everting hook 141, as schematically shown in FIGS. 2D and 2C for PMV 130 and 140 respectively, which anchor PMV 100 to a sub-annular tissue region in ventricle 42, on the underside of annulus 46, or just below the annulus along wall 49 of the ventricle.

Figure 5E:
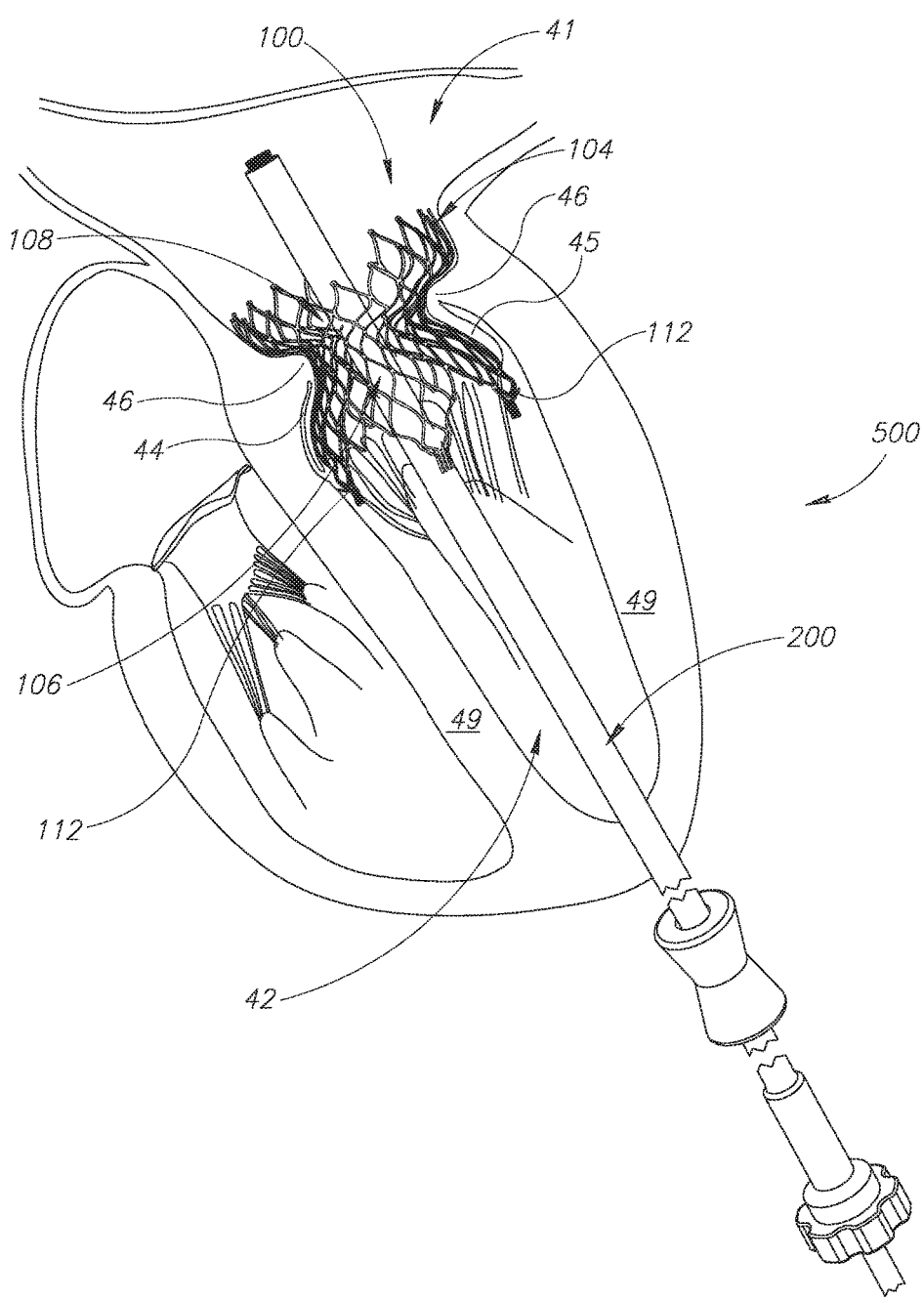
Figure 5F:
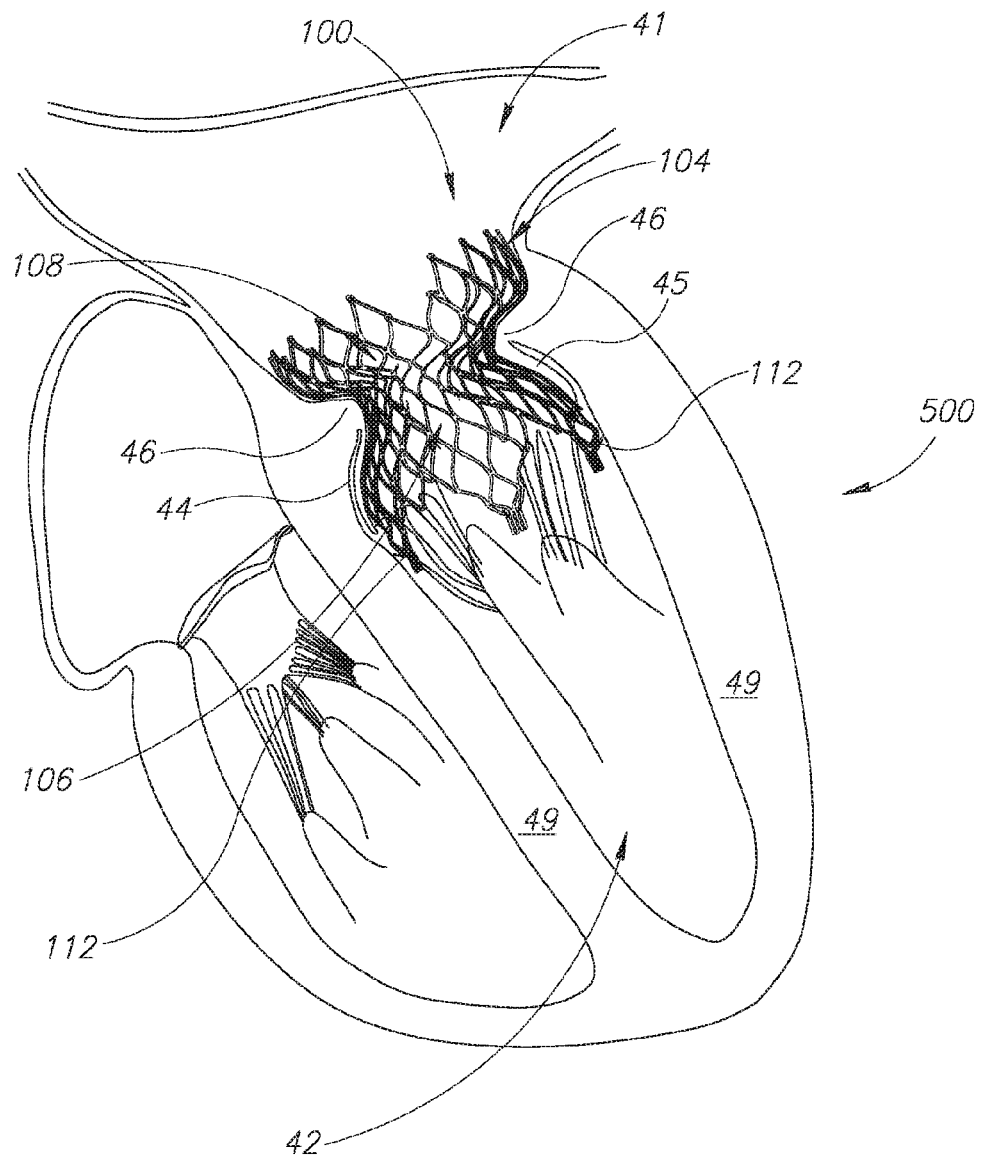

In FIG. 5E TDS 200 is operated to collapse scaffolding 250 back to its collapsed state as discussed with reference to FIG. 4D in preparation for removing TDS 200 from heart 500 while leaving PMV fully deployed. FIG. 5F schematically shows heart 500 after TDS 200 has been removed from heart 500.

Figure 6:
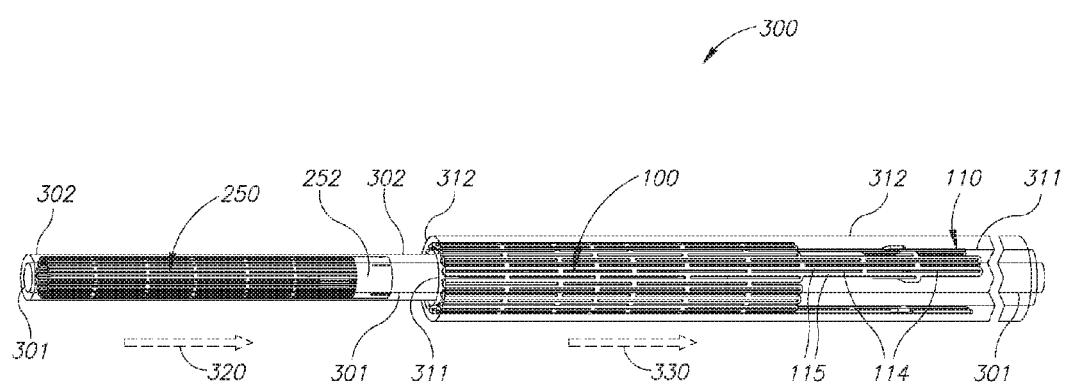
FIG. 6 schematically shows another TDS for deploying a PMV, in accordance with an embodiment of the invention.

FIG. 6 schematically shows an independent action TDS IA-TDS 300, for delivering and deploying a PMV, such as PMV 100 to replace a native mitral valve in accordance with an embodiment of the invention. IA-TDS 300 comprises inner and outer scaffolding control tubes 301 and 302 respectively for positioning and controlling release of scaffolding 250 from its collapsed state to an expanded state and inner and outer PMV control tubes 311 and 312 respectively for positioning and controlling release of PMV 100 from its collapsed state to its expanded state.

In its collapsed state as shown in FIG. 6, scaffolding 250 is concentric with and constrained in its collapsed state between inner and outer scaffolding control tubes 301 and 302. Scaffolding 250 is fixed to inner scaffolding control tube 301 optionally by fixing scaffold collar 252 to the inner scaffolding control tube. Outer scaffolding control tube 302 is controllable to be translated along inner scaffolding control tube 301. Translating outer scaffolding control tube in a proximal direction indicated by dashed arrow 320 releases scaffolding 250 to its expanded state, for example the expanded state schematically shown in FIG. 5C. Translating outer scaffolding control tube 302 so that it covers a portion but not all of scaffolding 250 distal to scaffolding collar 252 allows the scaffolding to partially expand. Scaffolding 250 expands to its fully expanded state when outer scaffolding control tube 302 is translated proximally so that the outer scaffolding control tube does not overlie any portion of scaffolding 250 distal of scaffolding collar 252.

PMV 100 is similarly constrained in its collapsed state between inner and outer PMV control tubes 311 and 312. Outer PMV control tube 312 is controllable to be translated along inner PMV control tube 311, and inner PMV control tube is translatable along outer scaffolding control tube 302. PMV 100 is held fixed to inner PMV control tube 311 by a configuration of small teeth (not shown) that releasably mesh with holes 114 in PMV 100 between struts 115 optionally in tails 110 of the PMV. As long as outer PMV control tube 312 is positioned to cover struts 115 and the small teeth, the teeth are constrained to mesh with the holes between the struts and PMV 100 is held fixed to inner PMV control tube 311.

Translating outer PMV control tube 312 in a proximal direction indicated by a dashed arrow 330 releases PMV 100 from its collapsed state to its expanded state. Translating outer PMV control tube 312 proximally so that it covers a portion, but not all of PMV 100, releases PMV 100 to partially expand, for example to partially expand to a partially expanded state shown in FIG. 5C in which upper cup 104 is expanded and lower cup 106 is not expanded. PMV 100 expands to its fully expanded state, such as shown in FIG. 5E, when outer PMV control tube 312 is translated proximally so that the outer PMV control tube 312 does not overlie any portion of PMV 100. Translating outer PMV control tube 312 proximally so that it no longer covers tails 110, releases the tails from the small teeth that mesh with holes 114 and struts 115 and completely releases PMV 100 from inner and outer PMV control tubes 311 and 312.

IA-TDS 300 enables positioning and deploying a PMV similar to PMV 100 independent of positioning and deploying a scaffolding, such as scaffolding 250, in a procedure to replace a native mitral valve with the PMV, in accordance with an embodiment of the invention.

Figure 7A:
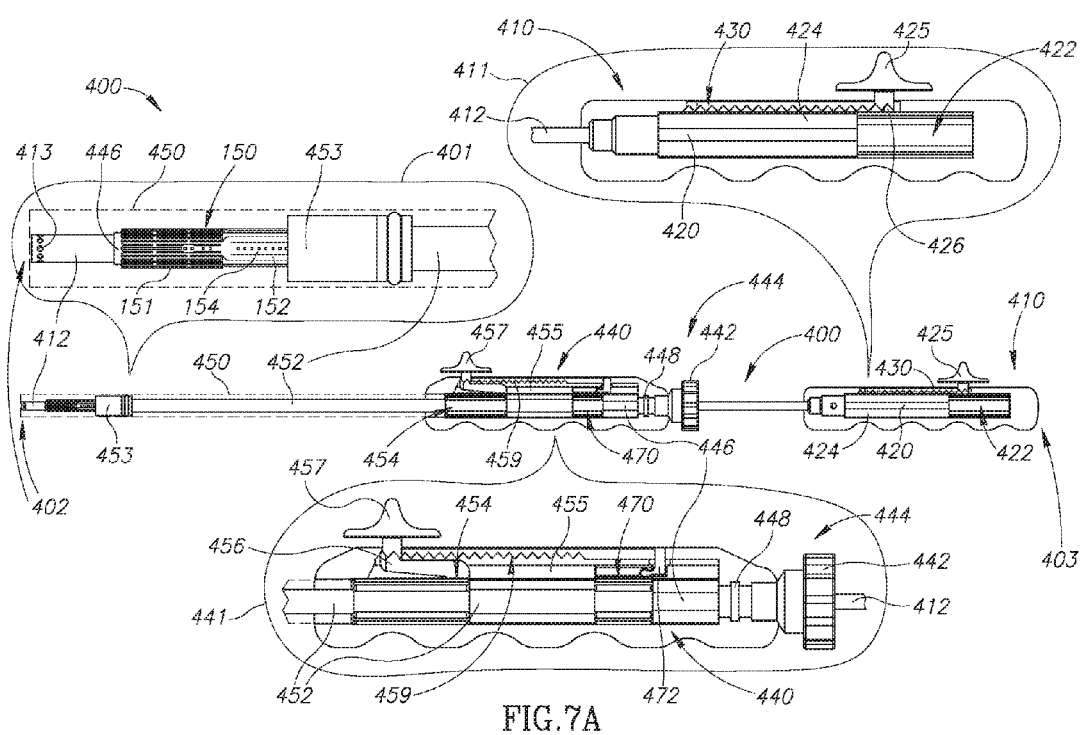
FIG. 7A schematically show components of an IA-TDS and relationships of the components, in accordance with an embodiment of the invention.

FIG. 7A schematically shows, partially cutaway, another IA-TDS, IA-TDS 400, for delivering and deploying an optionally self expanding PMV 150, in accordance with an embodiment of the invention. Optionally PMV 150 is a crown PMV.

IA-TDS 400 optionally comprises a scaffolding control handle 410, connected to a scaffolding housing tube 412 and a PMV deployment handle 440 that may be locked and sealed to scaffolding housing tube 412 by rotating a handle 442 of, optionally, a Touhy valve 444, coupled to the PMV handle. Scaffolding control handle 410 and PMV deployment handle 440 are shown cutaway, and in insets 411 and 441 respectively, enlarged for convenience of presentation. PMV 150 is mounted at a distal end 402 of IA-TDS 400 to a PMV delivery tube 446 and is shown enlarged in an inset 401. An end of IA-TDS 400 opposite distal end 402 may be referred to as a proximal end 403 of the IA-TDS.

PMV delivery tube 446 surrounds scaffolding housing tube 412 and is fixed to PMV deployment handle 440, optionally by fixing the PMV delivery tube to an o-ring housing 448, which seats in PMV deployment handle 440 and is optionally press fit to Touhy valve 444. A control sheath 450 and a PMV release tube 452 having a capture cup 453 are respectively coupled to PMV deployment handle 440 by slide carriages 454 and 470.

Slide carriage 454 to which control sheath 450 is coupled, is optionally a ratchet slide carriage that is translatable back and forth in a slide channel 455 formed in PMV deployment handle 440. Ratchet slide carriage 454 has a toothed lever arm 456 that is attached to a finger button 457 and engages a toothed rack 459 in slide channel 455. Finger button 457 protrudes out of PMV deployment handle 440 through a slot (not shown) in the handle. Ratchet slide carriage 454 may be translated in slide channel 455 by pressing down on finger button 457 to disengage ratchet slide carriage 454 from rack 459, moving finger button 457 to a desired location along slide channel 455, and releasing the finger button to reengage the ratchet slide carriage to rack 459 and lock the ratchet slide carriage in place. Control sheath 450 moves with ratchet slide carriage 454, and translation of carriage 454 back and forth in slide channel 455 translates control sheath 450 back and forth along PMV delivery tube 446 and PMV release tube 452.

PMV release tube 452 is coupled to a slide carriage 470 housed and translatable back and forth, in slide channel 455. Translation of slide carriage 470 in slide channel 455 translates PMV release tube 452 and its capture cup 453 along PMV delivery tube 412. Slide carriage 470, shown in cross section in inset 441, may be locked in slide channel 455 by a slide bolt 472 slidably mounted to PMV deployment handle 440, which couples to a slot in slide carriage 470.

PMV 150, which is shown in a collapsed state and mounted to PMV delivery tube 446 in FIG. 7A, is optionally a crown PMV comprising a crown wire mesh 151, hereinafter also a "crown mesh", tails 152 having anchor hooks 153 (shown in FIG. 7H but not in FIG. 7A), for anchoring the PMV to the left ventricle wall of a heart in which the PMV is deployed, and leaflet mounting struts 154 to which leaflets of the PMV are attached. PMV 150 is also shown in its collapsed state in FIG. 7C and in a deployed state in FIG. 7H. FIG. 7I schematically shows PMV 150 in the collapsed state greatly enlarged for convenience of viewing, and FIG. 7J shows PMV in its deployed state. FIG. 7K schematically shows a PMV 160 which is a variation of PMV 150.

PMV 150 is not released from its collapsed state as long as mesh crown 151 remains inside control sheath 150 and capture cup 453 remains cupping tails 152 and struts 154, as schematically shown in FIG. 7A. PMV 150 may be partially expanded by translating ratchet slide carriage 454 in PMV deployment handle 440 towards proximal end 403 to move control sheath 450 in proximal direction 403 sufficiently to uncover mesh crown 151 of PMV150 and allow the mesh crown to partially self expand. Moving slide carriage 470 in a proximal direction by operating figure button 457 to translate PMV release tube 452 and capture cup 453 proximally, releases tails 152 and struts 154 from capture cup 454 and allows PMV 150 to fully expand to a deployed state.

Distal end of scaffolding housing tube 412, located at distal end 402 of IA-TDS 400, is formed having scaffolding wire exit holes 413 through which, optionally shape memory, scaffolding wires 700 protrude to form a scaffolding for the left atrium 41 and leaflets 44 and 45 of mitral valve 43 (FIG. 1) during deployment of PMV 150. The scaffolding wires are not shown in FIG. 7A to facilitate discussion of details of distal end 402 OF IA-TDS 400. The scaffolding wires, their deployment and a scaffolding that they form in accordance with an embodiment of the invention are shown in FIGS. 7B-7H that follow, are referenced by reference number 700, and are discussed below with reference to the figures.

An amount by which the scaffolding wires protrude out of scaffolding housing tube 412 through exit holes 413 is controlled by a push rod 420 connected to a ratchet slide carriage 422 that is located in and translatable along a slide chamber 424 formed in scaffolding control handle 410. Ratchet slide carriage 422 has a finger button 425 having teeth 426, one of which is shown in inset 411, that engages a toothed rack 430 in scaffolding control handle 410. Ratchet slide carriage 422 may be translated in slide channel 424 by pressing down on finger button 425 to disengage ratchet slide carriage 422 from rack 430, moving the finger button to a desired location along slide channel 424, and releasing the finger button to reengage the ratchet slide carriage to rack 430 to lock the carriage in place. Push rod 420 moves with ratchet slide carriage 422 and translation of the slide carriage back and forth in slide channel 424 translates push rod 420 back and forth in scaffolding housing tube 412. Translation of ratchet slide carriage 422, and with it push rod 420, towards distal end 402 of IA-TDS 400 pushes scaffolding wires out of scaffolding housing tube 412 through exit holes 413 to form a scaffolding. Translation of ratchet slide carriage 422 and with it push rod 420 away from distal end 402 and towards proximal end 403 of IA-TDS 400 retracts the scaffolding wires through exit holes 413 into scaffolding housing tube 412 to collapse the scaffold.

Stages in operation of IA-DTS 400 and functioning of its components during deployment of PMV 150 are illustrated in FIGS. 7C-7H and discussed with reference to the figures. Direction of motion of components of IA-TDS 400 during a procedure to deploy PMV 100, is indicated by referencing the motion as being in the direction of distal end 402 of IA-TDS 400 or in the direction of the proximal end 403 of the IA-TDS. Deployment of PMV 150 in a heart is schematically illustrated in FIGS. 8A-8G

IA-TDS 400 is introduced into a patient's body and apically into the patient's heart in a state schematically shown in FIG. 7A, in which finger button 457 is maximally distal in PMV control handle 440, finger button 425 is maximally proximal in scaffolding control handle 410, and PMV 150 is in its collapsed state mounted to PMV delivery tube 446.

In FIG. 7B scaffolding handle 410 is moved distally towards PMV deployment handle 440 to push scaffolding housing tube 412 out of control sheath 450. After extending the scaffolding housing tube out of control sheath 450, the scaffolding control handle may be locked in place relative to PMV deployment handle 440 by rotating Touhy handle 442 to seal the PMV deployment handle to scaffolding housing tube 412.

In FIG. 7C finger button 425 of scaffolding control handle 410 and ratchet carriage 422 are displaced distally to move push rod 420 in scaffolding housing tube 412 toward distal end 402. Motion of push rod 420 in scaffolding housing tube 412 push scaffolding wires 700 to increase an amount by which they protrude out from the scaffolding housing via exit holes 413 shown in FIG. 7A, and optionally to form a small "umbrella" shape 701. The umbrella shape tends to prevent scaffolding wires 700 from getting caught and deformed on a region of the wall of the left atrium of a heart in which PMV 150 is being deployed during extension of the scaffolding wires to form a scaffolding that stabilizes the heart's left atrium and/or mitral valve. Features of distal end 402 of IA-TDS 400 and scaffolding wires 700 are shown enlarged in an inset 451.

FIG. 7D schematically shows finger button 425 translated distally beyond its position shown in FIG. 7C to increase an amount by which scaffolding wires 700 protrude out from scaffolding housing tube 412 and to form a scaffolding, hereinafter also referred to as a discus scaffolding 702, having an imaginary envelope in a shape reminiscent, optionally, of a thick discus like shape. A size of discus scaffolding 702 is matched to a size of a heart chamber in which it is to be used to advantageously stabilize the chamber and/or the TDS to facilitate performing a procedure in or adjacent to the chamber. Optionally the heart chamber is the left atrium. Optionally the procedure is a procedure to repair or replace the mitral valve.

FIG. 7E schematically shows finger button 425 translated to its maximum distal displacement toward distal end 402 to move push rod 420 in scaffolding housing tube 412 maximally distal and thereby extend scaffolding wires 700 to their maximum extension outside of scaffolding housing tube 412. When maximally extended, scaffolding wires 700 optionally form a scaffolding, hereinafter also referred to as a lampshade scaffolding 704, having an imaginary envelope in a shape reminiscent a lampshade. A size of lampshade scaffolding 704 is matched to a size of a heart chamber in which it is to be used to advantageously stabilize the chamber and/or the TDS to facilitate performing a procedure in or adjacent to the chamber. Optionally, the heart chamber is the left atrium. Optionally the procedure is a procedure to repair or replace the mitral valve. In 7E control sheath 450 and PMV release tube 452 have not been moved relative to PMV 150 and the PMV is in its collapsed state seated on PMV delivery tube 446 (FIG. 7C).

In FIG. 7F, finger button 457 is moved towards proximal end 403 to displace control sheath proximally and expose crown 151 of PMV 150 so that the PMV can partially expand. In FIG. 7F crown 151 is outside of lampshade scaffolding 704. A position of PMV 150 relative to a scaffolding, such as discus scaffolding 702 or lampshade scaffolding 704, provided by, optionally shape memory, scaffolding wires 700 may be determined by a relative position of scaffolding control handle 410 and PMV deployment handle 440. By changing a distance between them by moving PMV deployment handle 440 along scaffolding housing tube 412 and locking the PMV deployment handle to the scaffolding housing tube, the position of PMV 150 may be adapted to particular features of a patient's heart advantageous for deploying PMV 150.

Figure 7G:
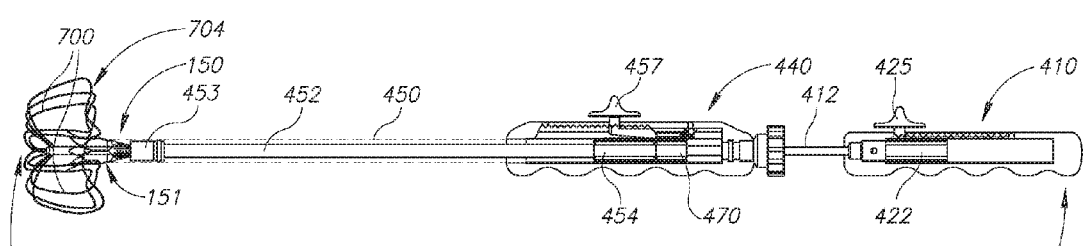

For example, as schematically shown in FIG. 7G, PMV 150 may be positioned inside landscape scaffolding 704 to be advantageously positioned for deployment in a patient's heart, by determining distance between PMV deployment handle 440 and scaffolding control handle 410. PMV 150 may be freed to fully self expand while inside lampshade scaffolding 704. During self expansion, PMV 150 pushes aside elements of lampshade scaffolding 704 that might interfere with proper expansion.

Figure 7H:
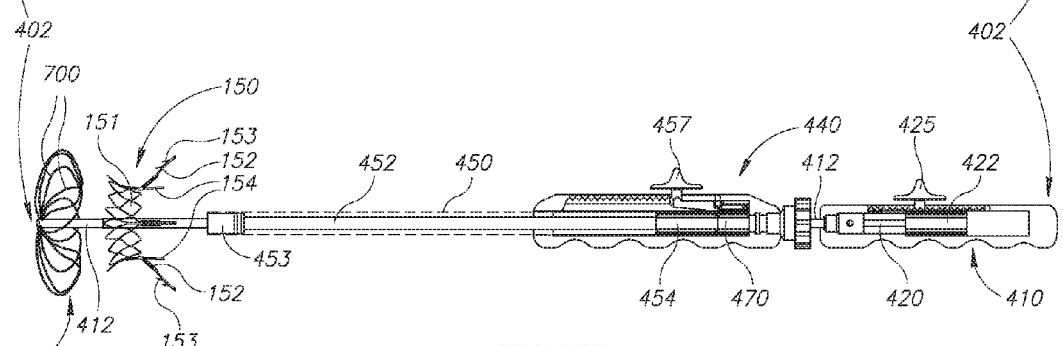
Figure 7I:
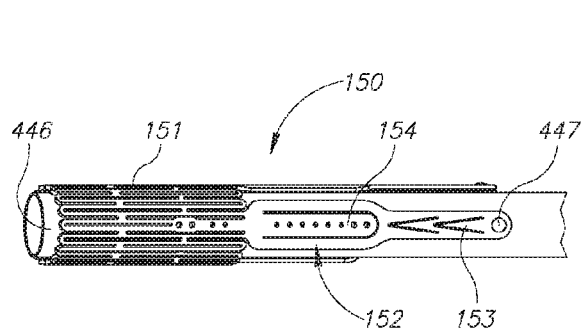
FIGS. 7I-7L, schematically show PMVs, in accordance with embodiments of the invention.
Figure 7J:
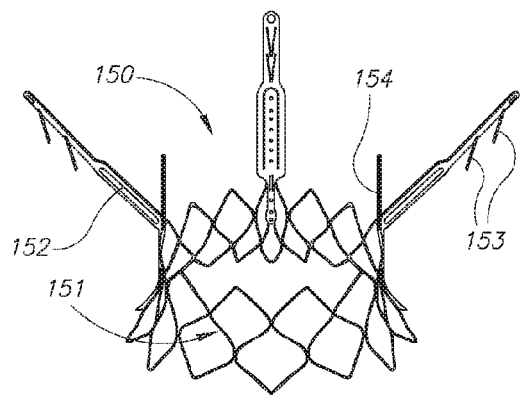
Figure 7K:
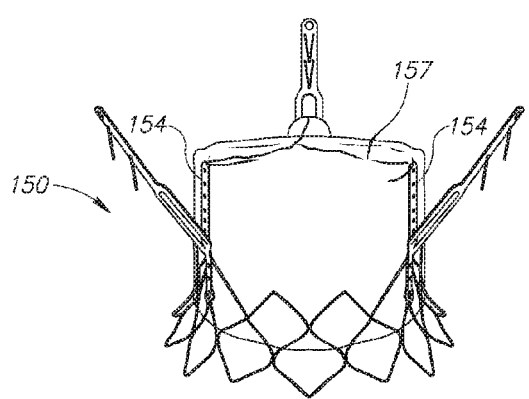

In FIG. 7H PMV 150 is schematically shown in a fully expanded deployed state, in accordance with an embodiment of the invention. Crown 151 is fully expanded and tails 152 splayed out to drive anchor hooks 153 into the wall 49 of ventricle 42 (shown in FIG. 8G, not in FIG. 7H) to anchor PMV 150 to a heart in which it is deployed. Expansion of PMV 150 is provided by moving finger button 457 to its maximal proximal position in PMV deployment handle 440. In moving finger button 457, ratchet slide carriage 454 contacts slide carriage 470 and both ratchet slide carriage 457 and slide carriage 470 move to their respective maximal proximal displacement, pulling with them control sheath 450 and release tube 452 respectively to their respective maximal proximal displacements. When maximally displaced proximally, control sheath 450 and release tube 452 do not constrain PMV 150 and the PMV self expands to its deployed state as shown in FIG. 7H. Following deployment of PMV 150 finger button 425 of scaffolding control handle 410 is moved proximally to retract push rod 20 and scaffolding wires 700 to collapse lampshade scaffolding 704 and prepare IA-TDS 400 for removal from a heart into which it has been introduced.

It is noted that positioning PMV 150 may be performed not only by determining its distance from a scaffolding provided by scaffolding wires 700, but also by rotating the PMV about an axis (not shown) of scaffolding housing tube 412. As schematically shown in FIG. 7I, PMV 150 is mounted to PMV delivery tube and held in place on the delivery tube optionally by nubs that prevent the PMV from rotating relative to the PMV delivery tube, which enables the PMV to be rotated to a rotational position in a patient's heart advantageous for deployment of the PMV.

FIGS. 7I and 7J schematically show enlarged images of PMV 150, in a collapsed state and fully deployed state respectively in accordance with an embodiment of the invention. As noted above and schematically shown in FIG. 7I PMV 150 is mounted to PMV delivery tube 446 and rotationally registered to the delivery tube optionally by nubs 447. Crown 151, tails 152 and their anchor hooks 153 are shown before being splayed out into their deployed state. Leaflet mounting struts 154 are nested in tails 152. When PMV 150 is in its expanded deployed state as schematically shown in FIG. 7J tails 152 and struts 154 are located at substantially same angular positions on crown 151. Optionally the tails and struts are symmetrically spaced around the circumference of crown 151 at angular intervals substantially equal to 120°. FIG. 7K schematically shows PMV 150 in its expanded state with leaflets 157 sewn to struts 154 and a portion of crown 151

Figure 7L:
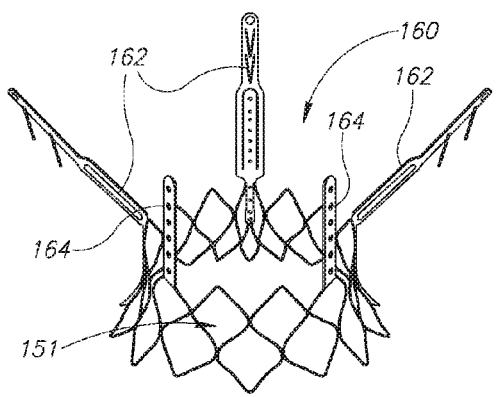

Whereas tails 152 and struts 154 comprised in PMV 150 are nested and symmetrically and evenly spaced around crown 151, PMVs in accordance with embodiments of the invention are not limited to nested, symmetric or evenly spaced tails and/or leaflet support struts. By way of example, FIG. 7L schematically shows a PMV 160 in accordance with an embodiment of the invention, comprising a crown 151, leaflet support struts 164 and tails 162. While leaflet support struts 164 are symmetrically and evenly spaced around crown 151, two support struts 164 are not nested in tails 162, and tails 162 are not evenly spaced around crown 151.

FIGS. 8A-8G schematically illustrate, as noted above, use of IA-TDS 400 in performance of a TAMVR procedure to replace a native mitral valve 43 of a heart 500 with PMV 150, in accordance with an embodiment of the invention.

Figure 8A:
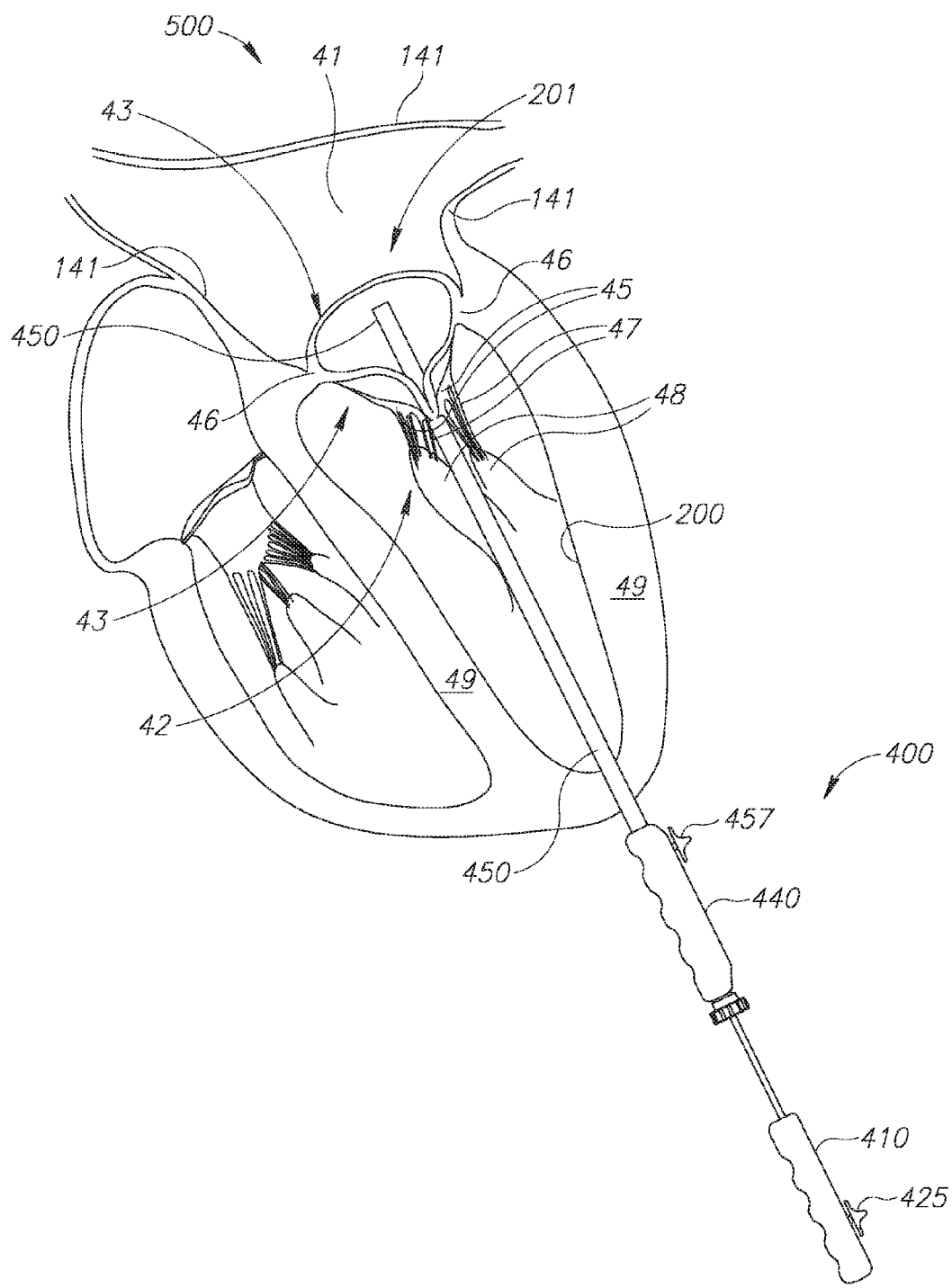
FIGS. 8A-8G schematically illustrate use of the IA-TDS shown in FIGS. 7A-7H to deploy a PMV in a heart, in accordance with an embodiment of the invention.

FIG. 8A schematically shows IA-TDS 400 at the beginning of the TAMVR procedure after a medical professional (not shown) such as a cardiac surgeon, has introduced IA-TDS 400 into a patient's heart 500 by puncturing the apex of heart 500 and navigating control sheath 450 through native mitral valve 43 so that it is positioned in left atrium 41. In FIG. 8A IA-TDS 400 is in a state as shown in FIG. 7A.

Figure 8B:
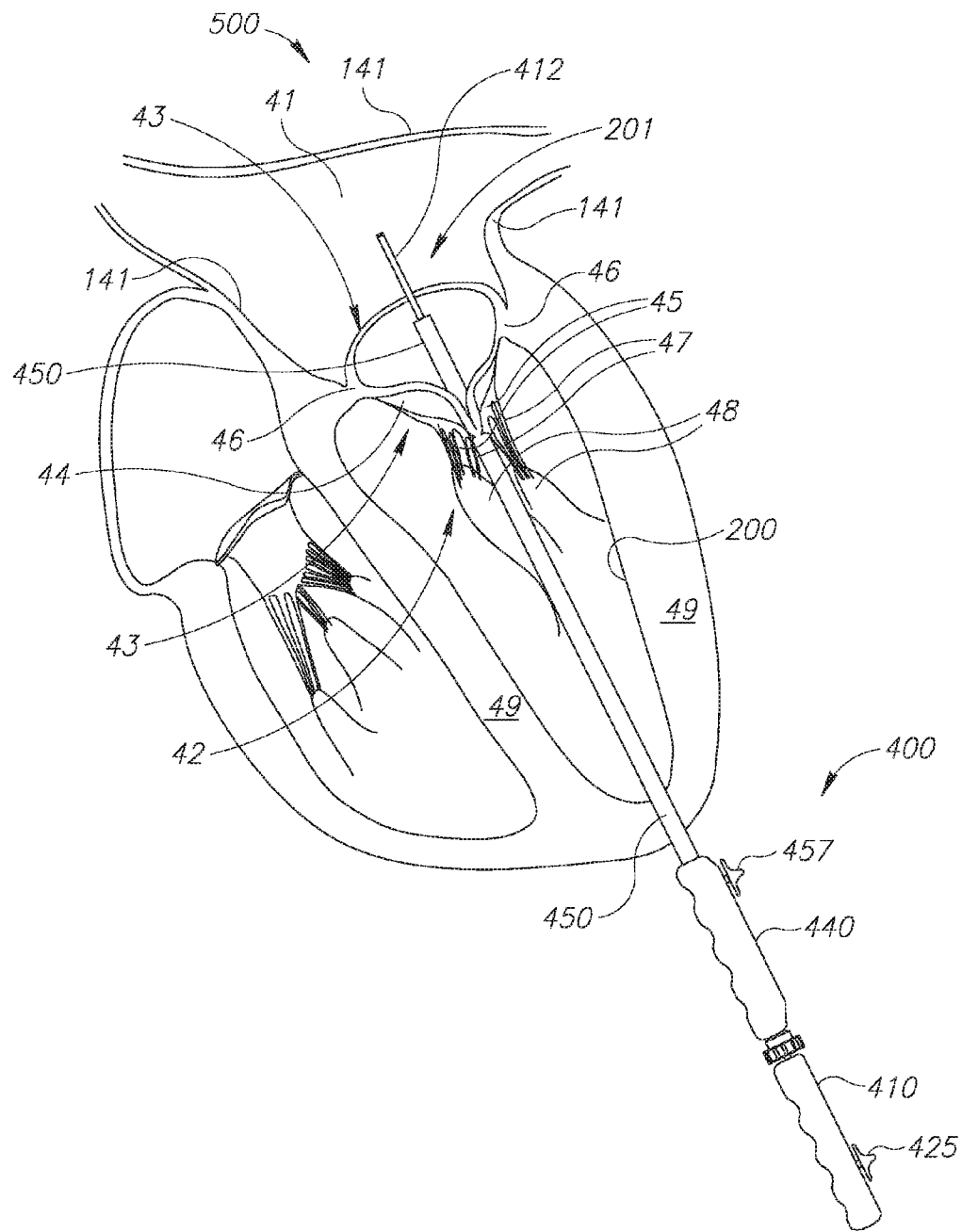
Figure 8C:
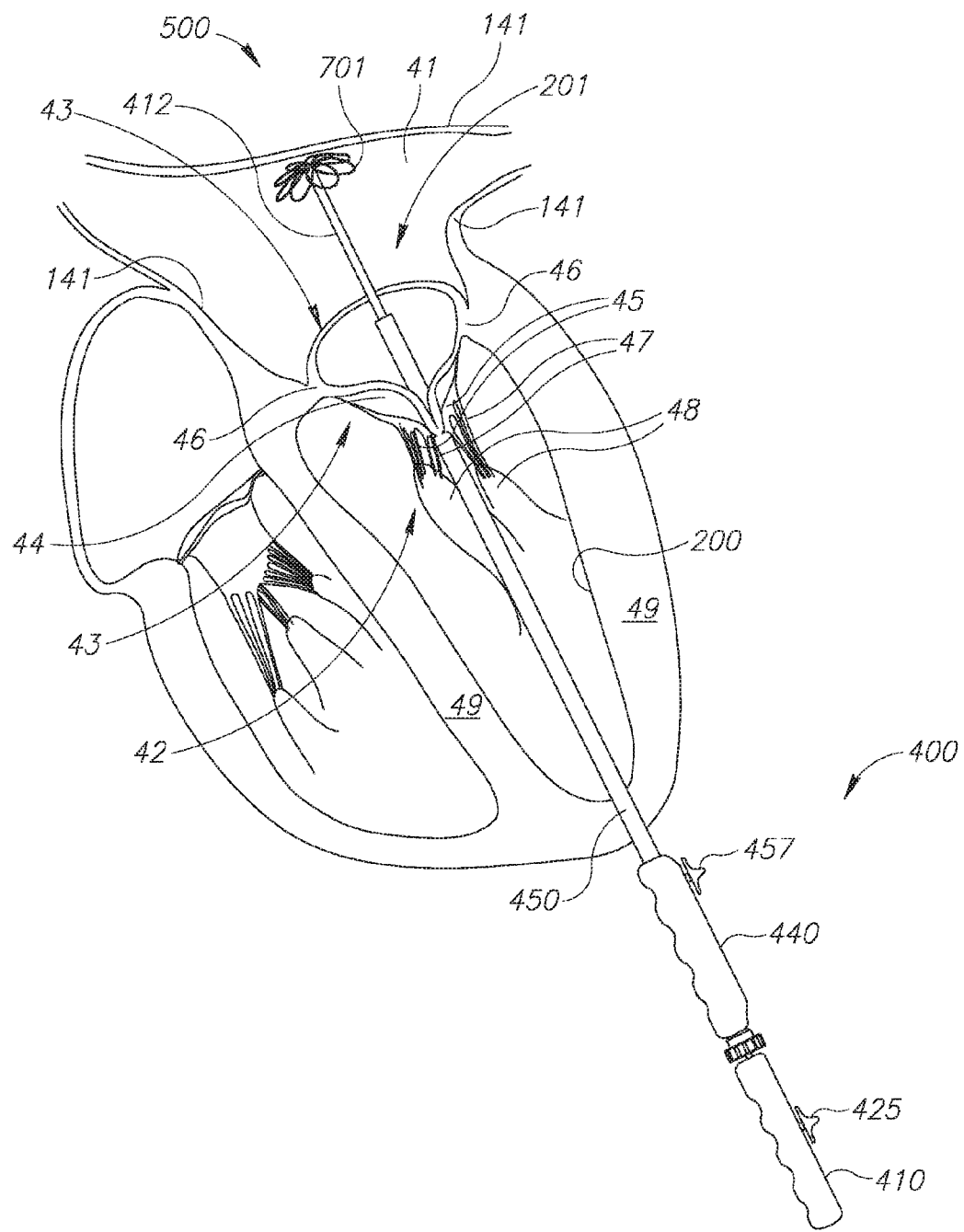
Figure 8D:
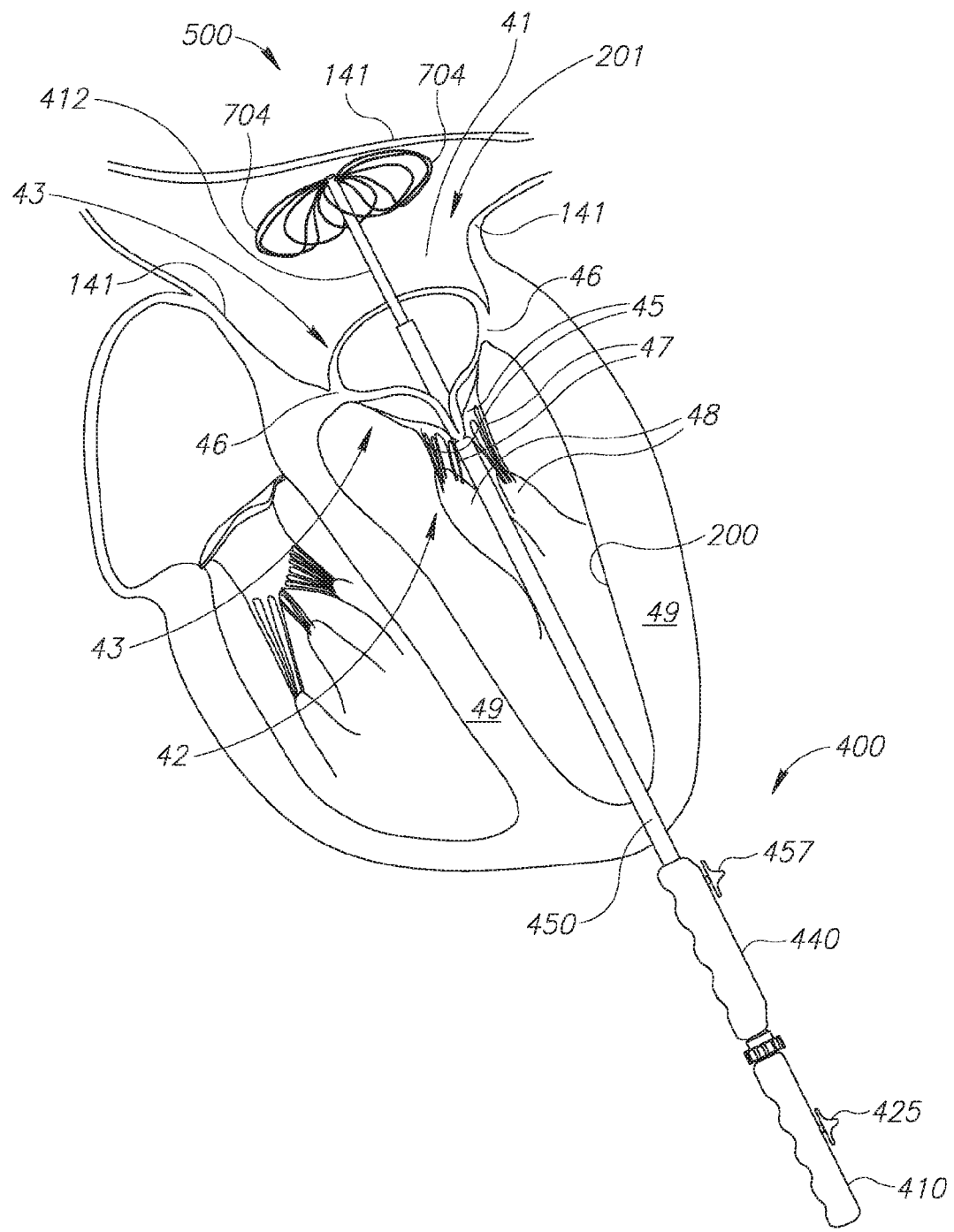
Figure 8E:
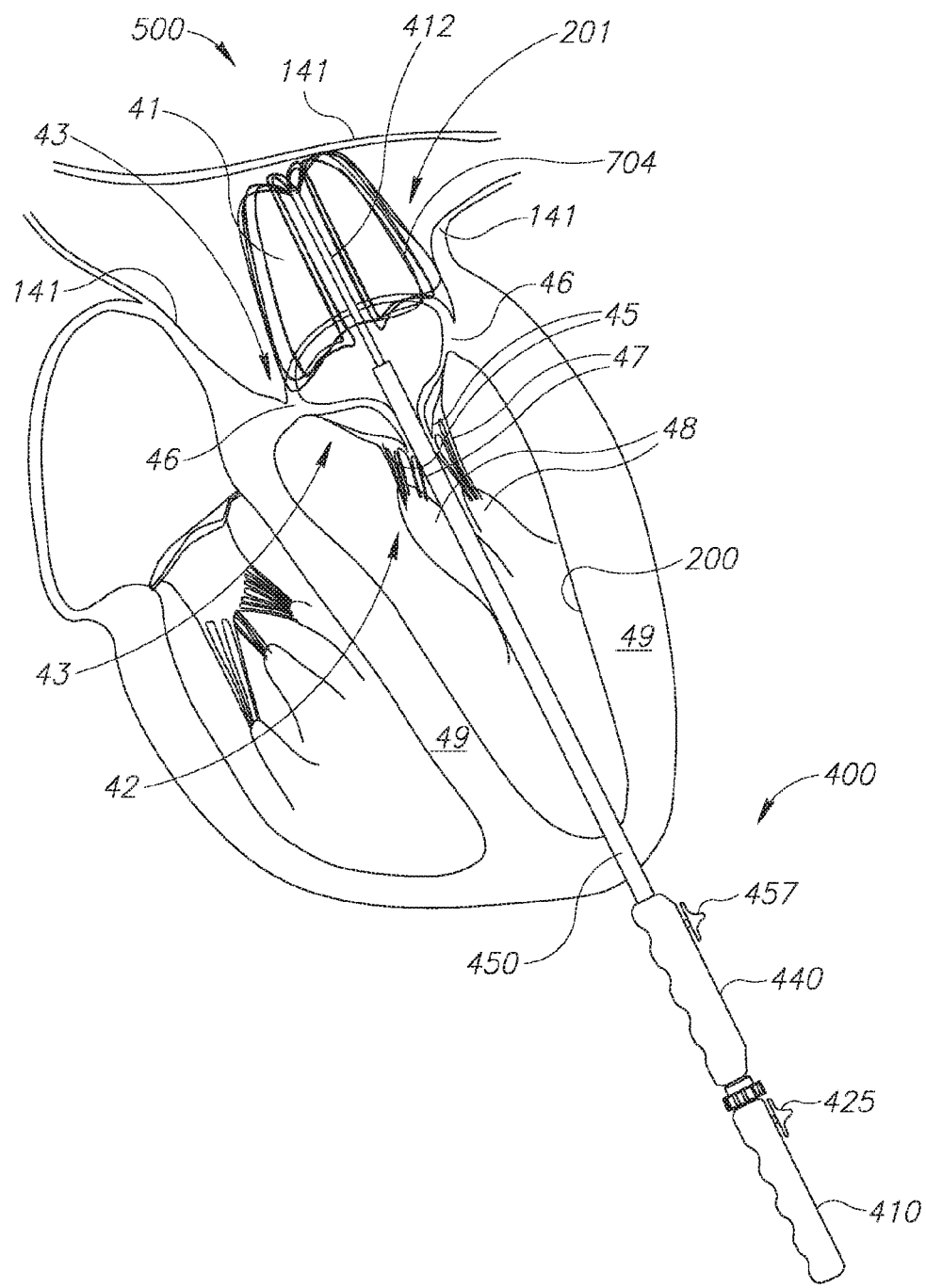

In FIG. 8B, scaffolding control handle 410 has been moved distally towards PMV deployment handle 440 to extend scaffolding housing tube 412 out from control sheath 450. IA-TDS 400 is in a state as shown in FIG. 7B. In FIGS. 8C and 8D scaffolding control handle 410 has been operated to deploy scaffolding wires 700 out from scaffolding housing tube 412 to respectively form umbrella 710 as shown in FIG. 7C and then discus scaffolding 702 as shown in FIG. 7D. Whereas discus scaffolding 702 may be advantageous for deploying PMV 150, the medical professional has determined that it is preferable to deploy a lampshade scaffolding 704 such as that discussed above with reference to FIGS. 7E-7G. FIG. 8E schematically shows scaffolding control handle having been operated to deploy lampshade scaffolding 704 in atrium 41 to stabilize the atrium and leaflets of mitral valve 43.

Figure 8F:
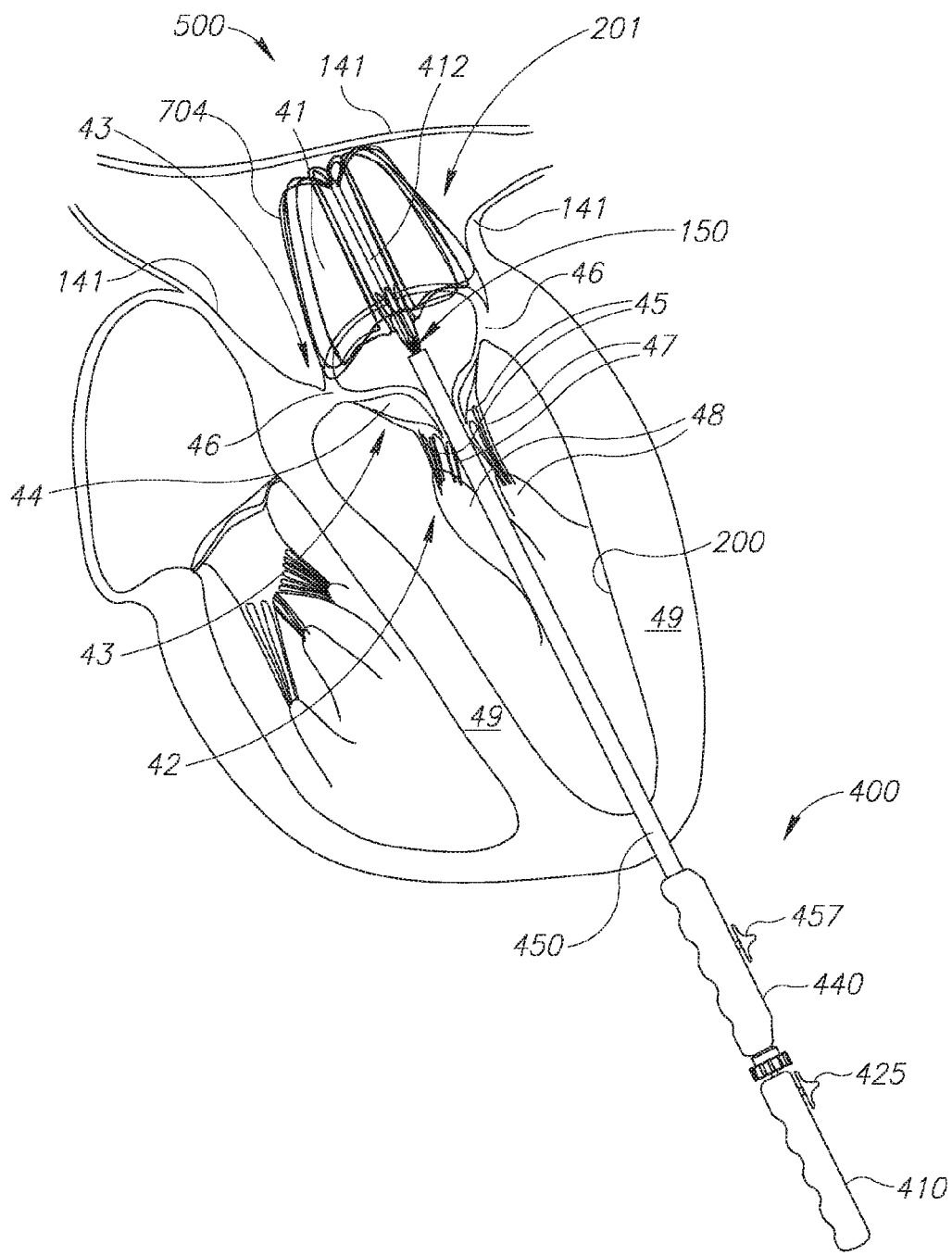

In FIG. 8F the medical professional has positioned PMV 150 inside lampshade scaffolding 704, a position similar to that discussed with respect to FIG. 7G, and operated PMV deployment handle 440 to partially expand PMV 150. While partially expanded, the medical professional is able to maneuver IA-TDS 450 to translate and/or rotate PMV 150 to determine a position of the PMV advantageous for replacing mitral valve 43 with PMV 150.

Figure 8G:
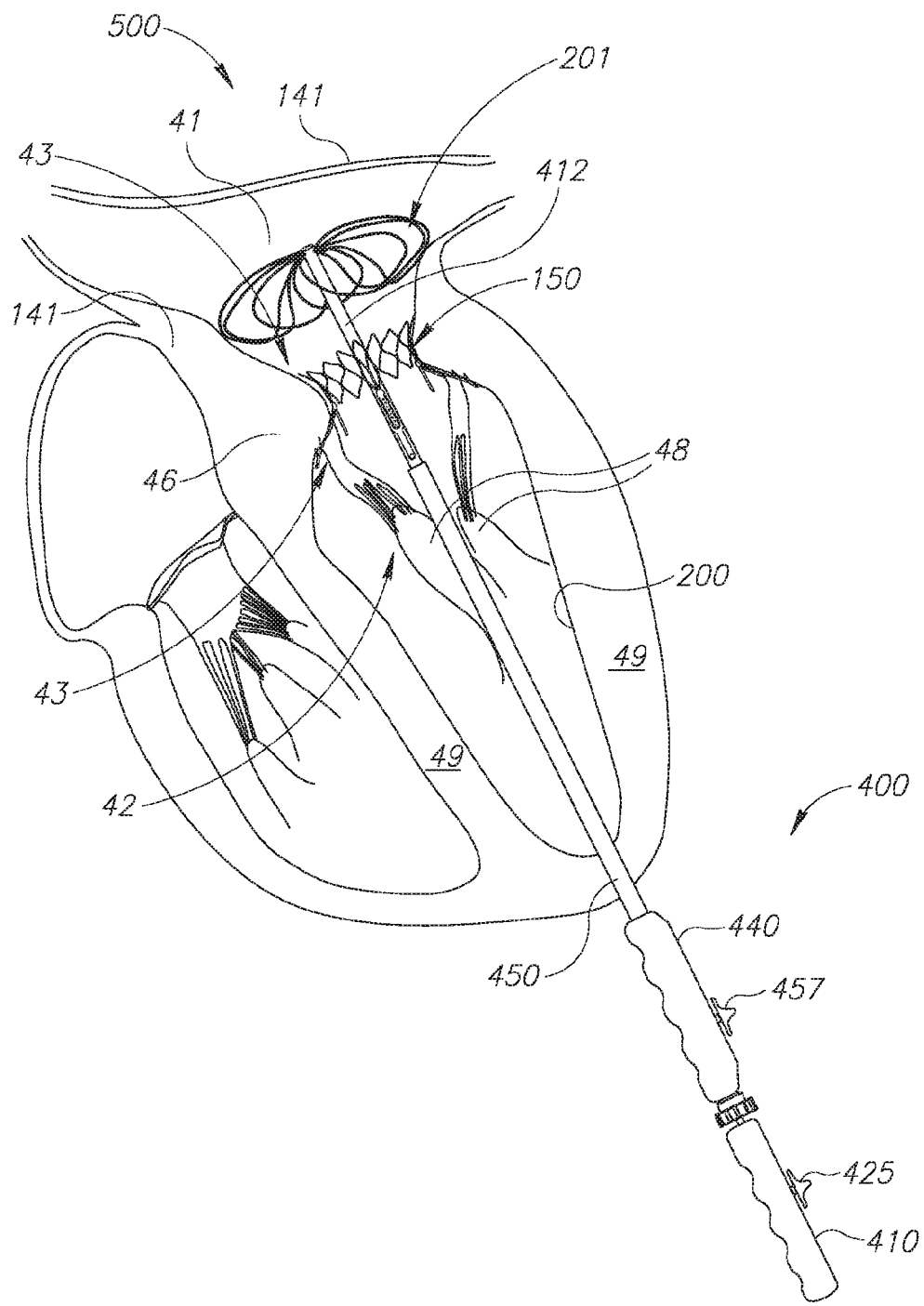

FIG. 8G schematically shows IA-TDS 400 after it has been operated to fully expand and deploy PMV 150 as a replacement for native mitral valve 43 and begin the procedure of collapsing scaffolding 704 in preparation of removing IA-TDS 400 from heart 500. The state of fully deployed PMV 150 and retraction of scaffolding wires 700 from lampshade scaffolding 704 shown in FIG. 8F to discus scaffolding 702 in FIG. 8G is similar to that discussed with reference to FIG. 7H.

It is noted that whereas IA-TDS 400 is described illustrated in FIGS. 8A-8g as being used to deploy PMV 150, use of IA-TDS 400 in accordance with an embodiment of the invention, is not limited to deployment of PMV 150. IA-TDS 400 may be used for example to deploy PMV 100, 130, 140 (FIGS. 2A, 2B, 2C) or PMV 160.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. Apparatus for replacing a native cardiac valve, the apparatus comprising:
   a wire mesh cardiac valve prosthesis having a cylindrical collapsed state and an expanded state and leaflets that operate to control blood flow;
   a wire mesh scaffolding having a collapsed state and at least one expanded deployed state configured to contact walls of a chamber in a heart on a retrograde side of the native cardiac valve and substantially fill the heart chamber;
   a delivery system comprising at least one tube in which the prosthesis and the scaffolding are mounted in their collapsed state that is controllable to:
   deploy the scaffolding in its expanded state on the retrograde side of the native valve;
   deploy the prosthesis in its expanded state; and
   remove the scaffolding in the collapsed state from the site of the native cardiac valve to leave the deployed prosthesis replacing the native valve.

2. The apparatus according to claim 1 wherein the at least one tube comprises a scaffolding housing tube formed having exit holes at a distal end thereof and in the collapsed state the wire mesh scaffolding comprises a plurality of scaffolding wires housed in the scaffolding housing tube, each of which scaffolding wires extends out from the scaffolding housing tube through two of the exit holes to form a small loop outside of the scaffolding housing tube.

3. The apparatus according to claim 2 and comprising a push rod inside the scaffolding housing tube that is connected to the scaffolding wires and is slidable inside the scaffolding housing tube to push and pull on the scaffolding wires to respectively increase or decrease the size of the loops outside of the scaffolding housing tube.

4. The apparatus according to claim 3 wherein the push rod is operable to push the scaffolding wires through the exit holes out from the scaffolding housing tube to form loops that cooperate to form the at least one expanded deployed state of the wire mesh scaffolding.

5. The apparatus according to claim 4 wherein the at least one expanded deployed state of the wire mesh scaffolding comprises a plurality of different expanded deployed states that the loops cooperate to form as a function of the size of the loops.

6. The apparatus according to claim 5 wherein the plurality of different expanded deployed states comprises a state in which the loops have an envelope in a shape of a discus.

7. The apparatus according to claim 5 wherein the plurality of different expanded deployed states comprise a state in which the loops have an envelope in a shape of a lampshade.

8. The apparatus according to claim 2 wherein the at least one tube comprises a prosthesis delivery tube that surrounds the scaffolding housing tube and to which prosthesis delivery tube the cardiac valve prosthesis is mounted in the collapsed state.

9. The apparatus according to claim 8 wherein the at least one tube comprises a release tube surrounding the prosthesis delivery tube that constrains at least a portion of the cardiac valve prosthesis to prevent the cardiac valve prosthesis from self expanding to the expanded state.

10. The apparatus according to claim 9 wherein the release tube is translatable relative to the prosthesis delivery tube to cease constraining the at least portion of the cardiac valve prosthesis.

11. The apparatus according to claim 9 wherein the at least one tube comprises a control sheath surrounding the release tube that constrains at least a portion of the cardiac valve prosthesis to prevent the cardiac valve prosthesis from self expanding to the expanded state.

12. The apparatus according to claim 11 wherein the control sheath is translatable relative to the prosthesis delivery tube to cease constraining the at least portion of the cardiac valve prosthesis.

13. The apparatus according to claim 1 wherein the prosthesis in the expanded state comprises:
   a mesh crown;
   a plurality of tails attached to the mesh crown that are splayed out and comprise hooks configured to puncture and anchor into tissue on the antegrade side of the native valve; and
   a plurality of support struts attached to the crown that support the leaflets and are substantially not splayed out.

14. The apparatus according to claim 13 wherein the tails and support struts are located at substantially same angular locations on the crown.

15. The apparatus according to claim 13 wherein the tails and support struts are located at different angular locations on the crown.

16. The apparatus according to claim 1 wherein the cardiac valve prosthesis has a cinch-girdle expanded state in which the prosthesis comprises upper and lower cups joined at a relatively narrow waist and when deployed the upper cup and lower cups are located respectively on retrograde and antegrade sides of the native cardiac valve.

17. The apparatus according to claim 16 wherein the at least one tube comprises a delivery tube to which the scaffolding and prosthesis are mounted.

18. The apparatus according to claim 17 wherein in their collapsed states a portion of the prosthesis overlaps a portion of the scaffolding.

19. The apparatus according to claim 18 and comprising a prosthesis control tube concentric with the delivery tube that constrains a portion of the prosthesis to its constrained state and is translatable along the delivery tube to release the constrained portion to expand towards the expanded state.

20. The apparatus according to claim 19 and comprising a control sheath concentric with the delivery tube and the prosthesis control tube that constrains the scaffolding and the portion of the prosthesis that overlies the scaffolding to their collapsed states and is translatable along the prosthesis control tube to release the scaffolding and the portion of the prosthesis overlying the scaffolding to expand towards their expanded states.

* * * * *